(12) United States Patent
Nishiuchi et al.

(10) Patent No.: US 8,253,113 B2
(45) Date of Patent: Aug. 28, 2012

(54) CHARGED PARTICLE BEAM IRRADIATION SYSTEM AND CHARGED PARTICLE BEAM EXTRACTION METHOD

(75) Inventors: Hideaki Nishiuchi, Hitachinaka (JP);
Kazuyoshi Saito, Hitachi (JP);
Masahiro Tadokoro, Hitachiohta (JP);
Hiroshi Akiyama, Hitachiohta (JP);
Kazuo Hiramoto, Hitachiohta (JP)

(73) Assignee: Hitachi, Ltd., Tokyo (JP)

( * ) Notice: Subject to any disclaimer, the term of this patent is extended or adjusted under 35 U.S.C. 154(b) by 593 days.

(21) Appl. No.: 12/490,696

(22) Filed: Jun. 24, 2009

(65) Prior Publication Data

US 2010/0001212 A1    Jan. 7, 2010

(30) Foreign Application Priority Data

Jul. 2, 2008   (JP) .................. 2008-173451

(51) Int. Cl.
    *G21K 5/04*          (2006.01)
(52) U.S. Cl. ................. 250/396 R; 250/397; 250/492.1; 250/492.3; 315/500; 315/503
(58) Field of Classification Search ............. 250/396 R, 250/397, 492.1, 492.3; 315/500, 501, 503; 600/1, 2
See application file for complete search history.

(56) References Cited

U.S. PATENT DOCUMENTS

| | | | |
|---|---|---|---|
| 5,363,008 | A | 11/1994 | Hiramoto et al. |
| 6,873,123 | B2 | 3/2005 | Marchand et al. |
| 7,439,528 | B2 * | 10/2008 | Nishiuchi et al. .......... 250/492.3 |
| 2004/0155206 | A1 | 8/2004 | Marchand et al. |
| 2005/0231138 | A1 | 10/2005 | Nakanishi et al. |
| 2006/0226372 | A1 * | 10/2006 | Yanagisawa et al. ..... 250/396 R |
| 2007/0158592 | A1 | 7/2007 | Hiramoto et al. |
| 2007/0228291 | A1 | 10/2007 | Hiramoto et al. |
| 2007/0228304 | A1 | 10/2007 | Nishiuchi et al. |

FOREIGN PATENT DOCUMENTS

EP        0 994 638 A1     4/2000

(Continued)

OTHER PUBLICATIONS

Chu et al., "Instrumentation for treatment of cancer using proton and light-ion beams", Review of Scientific Instruments vol. 64(8), 1993.*
W.T. Chu et al., Instrumentation for treatment of cancer using proton and light-ion beams, Review of Scientific Instruments, vol. 64, No. 8, Aug. 1993, pp. 2055-2122.

(Continued)

*Primary Examiner* — David A Vanore
*Assistant Examiner* — Nicole Ippolito
(74) *Attorney, Agent, or Firm* — Mattingly & Malur, PC

(57) ABSTRACT

A charged particle beam irradiation system includes a synchrotron which accelerates an ion beam, an irradiation apparatus for irradiating an object with the ion beam introduced from the synchrotron, detection means for measuring an amount of accumulated charge of the ion beam that orbits in the synchrotron immediately before an extraction control period in an operating cycle of the synchrotron, and beam extraction control means for controlling extraction of the ion beam based on the measurement result of the accumulated beam charge amount so that extraction of a total amount of the ion beam is to be completed with an expiration of an extraction control time, the extraction control time representing a length of the extraction control period of the synchrotron and being set in advance.

26 Claims, 11 Drawing Sheets

FOREIGN PATENT DOCUMENTS

| | | |
|---|---|---|
| EP | 1 656 966 A1 | 5/2006 |
| EP | 1 733 757 A2 | 12/2006 |
| EP | 1 826 778 A2 | 8/2007 |
| JP | 2596292 B2 | 1/1997 |
| JP | 9-330800 A | 12/1997 |
| JP | 2004-529483 A | 9/2004 |
| JP | 2005-129548 A | 5/2005 |
| JP | 2006-239404 A | 9/2006 |
| JP | 2007-260193 A | 10/2007 |

OTHER PUBLICATIONS

T. Furukawa et al., Global spill control in RF-knockout slow extraction, Nuclear Instruments and Method in Physics Research A 522, 2004, pp. 196-204.

T. Furukawa et al., Design study of a raster scanning system for moving target irradiation in heavy-ion radiotherapy, Medial Physics, vol. 34, No. 3, Mar. 2007, pp. 1085-1097.

* cited by examiner

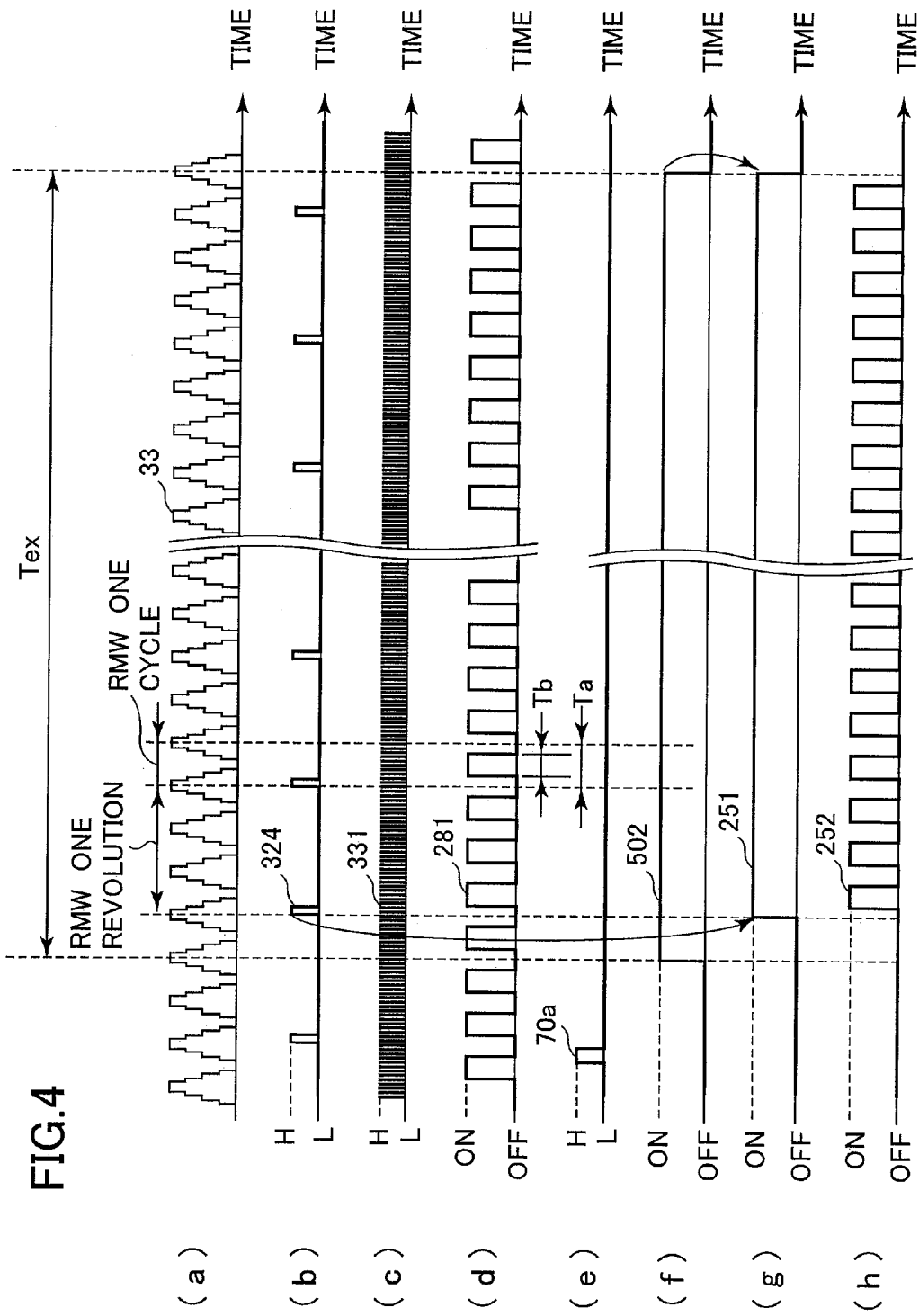

CHARGED PARTICLE BEAM IRRADIATION SYSTEM AND CHARGED PARTICLE BEAM EXTRACTION METHOD

BACKGROUND OF THE INVENTION

1. Field of the Invention

The present invention relates to a charged particle beam irradiation system and charged particle beam extraction method. More particularly, the present invention relates to a charged particle beam irradiation system and a charged particle beam extraction method that are ideally adaptable to a particle therapy system that treats a cancer by irradiating an affected part (an object to be irradiated) with a charged particle beam (ion beam) such as a proton or a heavy ion.

2. Description of the Related Art

A particle therapy method is known as a radiation therapy for cancers, in which a cancer affected part of a patient is irradiated with an ion beam such as, for example, a proton or heavy ion beam. A particle therapy system used in such a therapy may include an ion beam generator, a beam transport line, and an irradiation apparatus. The ion beam generator includes a synchrotron or a cyclotron that accelerates the ion beam that orbits along a circular path and thereby increases its energy to a required level.

The synchrotron includes a radiofrequency acceleration system (acceleration cavity), an extraction radiofrequency electrode, and an extraction deflector (see, for example, JP 2596292 B2). Specifically, the radiofrequency acceleration system accelerates the ion beam that orbits along a circular path to a target level of energy by feeding a radiofrequency voltage to the ion beam. The extraction radiofrequency electrode augments a betatron oscillation amplitude of the orbiting ion beam. The extraction deflector takes the ion beam out of the circular path. When the ion beam which has been accelerated to the target level of energy is to be extracted from the synchrotron to the beam transport line, a radiofrequency magnetic field or a radiofrequency electric field (hereinafter referred to as a radiofrequency signal) is fed to the extraction radiofrequency electrode to thereby augment the betatron oscillation amplitude that is the natural oscillation of the orbiting ion beam. The ion beam with the augmented betatron oscillation amplitude moves out of a stability limit, and is extracted from the synchrotron to the beam transport line and transported onto the irradiation apparatus.

The irradiation apparatus shapes the ion beam, which is introduced from the ion beam generator, in accordance with the depth of the affected part from a patient's body surface and the shape of the affected part and irradiates the affected part of the patient on a treatment couch with the shaped ion beam. The irradiation apparatus irradiates the affected part with the ion beam by using an appropriate beam irradiation method. In general, the irradiation apparatus uses a double scatter method (see page 2081, FIG. 35 of non-patent document 1, Review of Scientific Instruments, vol. 64, no. 8 (August 1993), pages 2074 to 2093), RMW irradiation method (see page 2077, FIG. 30 of non-patent document 1), wobbler method (see page 2084, FIG. 41 of non-patent document 1), or beam scanning method (see pages 2086 to 2090 of non-patent document 1 and page 197 of non-patent document 2, Nuclear Instruments and Method in Physics Research Section A, 522 (2004), pages 196 to 204). A raster beam scanning method (see pages 2087 to 2089 of non-patent document 1) is available as a type of the beam scanning method.

The affected part usually has a certain thickness in the direction of the ion beam traveling in a patient body. To irradiate the entire thickness of the affected part with the ion beam, the energy of the ion beam must be controlled so as to form a uniform absorbed dose range (spread-out Bragg peak; hereinafter abbreviated to SOBP) having a certain width in the ion beam traveling direction. A scattering irradiation method that uses a range modulation wheel (hereinafter referred to as the RMW) is proposed as an energy control means for forming a desired SOBP. The RMW is a rotating structure having a plurality of wedge-shaped energy absorbers disposed in a circumferential direction so that the thickness of a region through which the ion beam passes varies with time. The RMW is arranged such that the thickness in the ion beam traveling direction (the axial direction of the RMW) increases or decreases as the RMW rotates. Such an irradiation method as that which uses the RMW is called an RMW irradiation method.

The irradiation apparatus shapes the ion beam in accordance with the depth from the patient's body surface and the shape of the affected part. The current intensity of the beam incident on the affected part is, however, adjusted by the ion beam generator. In the synchrotron, the beam current intensity of the ion beam extracted from the ion beam generator is controlled by adjusting the intensity of the radiofrequency signal (amplitude of the radiofrequency voltage) to be fed to the extraction radiofrequency electrode (non-patent document 2). The cyclotron, on the other hand, includes a device that adjusts the intensity of an extracted ion beam (see, for instance, JP 2004-529483 A). More specifically, the cyclotron measures the intensity of an actually extracted beam and controls an arc current that is to be supplied to an ion source based on the measurements.

The synchrotron receives the injected ion beam from a preaccelerator, accelerates the injected ion beam to a desired level of energy, and extracts the accelerated ion beam. The synchrotron repeatedly performs one cycle of operations that includes injecting an ion beam, accelerating the injected ion beam, and extracting the accelerated ion beam. Unlike the supply of ion beams to the cyclotron, therefore, the ion beam is supplied to the synchrotron only at the time of injecting the ion beam within one operating cycle. The amount of accumulated charge of ion beams accelerated by the synchrotron is maximized at the end of acceleration and decreases with the lapse of the extraction control time (non-patent document 1). Further, it is known that the relationship between the amplitude of the radiofrequency signal to be fed to the extraction radiofrequency electrode and the beam current intensity extracted from the synchrotron is also affected by the accumulated beam charge amount within the synchrotron. In non-patent document 3, Medical Physics, vol. 34, no. 3, March 2007, pages 1085 to 1097, therefore, an amplitude modulation waveform of an extraction radiofrequency signal required for making constant a change with time in the beam current intensity is provided based on an estimation made of the decrease in the accumulated beam charge amount in the synchrotron as the beam extraction control is performed. To minimize effect from fluctuations in the accumulated beam charge amount in the synchrotron, the accumulated beam charge amount in the synchrotron is measured with a DC current transformer (DCCT) and, in accordance with the measurement, a target intensity of the extraction beam current is set. In addition, to suppress a ripple component produced in the extraction beam, feedback control is applied relative to the amplitude modulation waveform of the extraction radiofrequency signal based on the current intensity of the extraction beam observed on a beam ripple monitor. Non-patent document 3 also proposes, in the beam scanning irradiation method, to set a required value of the extracted beam current intensity corresponding to a beam extraction gate width which is defined from the average breathing cycle of the patient measured in advance.

In the RMW irradiation method, on the other hand, a technique is known (JP 2006-239404 A), by which desired SOBP formation can be achieved by controlling the thickness of a periodic structure of the RMW through which the beam passes in order to allow a single RMW to respond to a plurality of patients. Specifically, the thickness of the RMW through which the beam passes is controlled by performing ON/OFF control of the extraction beam in accordance with the thickness of the periodic structure of the RMW adapted to the desired SOBP formation. When the synchrotron is applied to the ion beam generator of the charged particle beam irradiation system, the ON/OFF control of the extraction beam can be achieved by performing the ON/OFF control of the radiofrequency signal fed to the extraction radiofrequency electrode.

SUMMARY OF THE INVENTION

The prior-art techniques have the following problems.

The scattering irradiation method including the RMW irradiation method is required to offer a beam irradiation therapy at a higher dose rate than the beam scanning irradiation method, so that a need arises to fire as many beams accumulated in the synchrotron as possible. When, in the RMW irradiation method disclosed in JP 2006-239404 A, the ON/OFF control of the extraction beam is performed on areas required for SOBP formation, on the other hand, a beam irradiation time per one operating cycle of the synchrotron is limited. Specifically, a rate of a beam extraction control time (the time hereinafter referred to as the beam ON control time and the rate hereinafter referred to as the beam use efficiency) is reduced relative to an extraction-enabled control time within the operating cycle of the synchrotron. The narrower the desired SOBP width, the lower the beam use efficiency, so that the accumulated charge of ion beams in the synchrotron cannot be fired effectively. The RMW irradiation method does not therefore allow the beam use efficiency to be enhanced by simply controlling the amplitude of the extraction radiofrequency voltage according to the accumulated beam charge amount before the start of the extraction control. To enhance the beam use efficiency while performing the ON/OFF control of the extraction beam, it is necessary that the amplitude of the extraction radiofrequency voltage be controlled based on the accumulated beam charge amount before the start of the extraction control and the beam ON control time.

Non-patent document 3 discloses a technique relating to the beam scanning irradiation method, in which the intensity of the extraction beam is controlled in accordance with the scanning trajectory length during beam scanning irradiation; specifically, the intensity of the extraction beam is controlled to be low when the scanning trajectory length is short and high when the scanning trajectory length is long. Non-patent document 3 does not, however, mention the amplitude control for the extraction radiofrequency signal in consideration of the extraction beam ON/OFF control required for SOBP formation, as required in the RMW irradiation method.

The RMW used in the RMW irradiation method disclosed in non-patent documents 1 and 2 includes a plurality of wedge-shaped energy absorbers disposed symmetrically about a revolving axis to form a periodic structure. It is therefore necessary to fire the ion beam symmetrically so as to match with the symmetrical configuration of the wedge-shaped energy absorbers. When, in this case, the accumulated beam charge amount in the synchrotron is smaller than a reference value, the accumulated charge of ion beams in the synchrotron is exhausted during irradiation; when the beam irradiation is terminated halfway through the range of angles to be irradiated, uniformity of irradiation dose can no longer be maintained. To maintain uniformity of the irradiation dose, it is required to maintain the supply of beams without exhausting the beams until a predetermined region (portion of a predetermined depth) is completely irradiated with the beam during the ON control.

Even with the raster beam scanning method as a type of the scanning method and the wobbler method described in non-patent documents 1 and 2, it is required to maintain the supply of beams without exhausting the beams until a predetermined region is completely irradiated with the beam during the extraction control.

In the raster beam scanning method, the irradiation of the affected part in the depth direction is controlled with the beam energy supplied from the accelerator system. When the entire thickness of the affected part is to be irradiated with the beam, it is required that the beam current intensity be controlled at a predetermined level at all times so as to maintain uniformity of the irradiation dose. The irradiation depth surface should therefore be irradiated at least at one time in the extraction control period in the synchrotron.

In the wobbler method, a scatterer is irradiated with a circularly scanning beam to form the SOBP adapted to the affected part. At this time, a beam irradiation start point must coincide with an end point to ensure uniformity of the irradiation dose. Further, when the change with time in the current intensity of the circularly scanning beam fluctuates, uneven uniformity results in the irradiation dose on a plane of an irradiation field. Specifically, uniformity of the irradiation dose can be ensured by making the beam circular scanning cycle coincide with the beam extraction cycle in the extraction control period of the synchrotron.

As described above, to ensure uniformity of the irradiation dose by using the raster beam scanning method or the wobbler method, the beam extraction control must be performed with care not to allow the change with time in the beam current intensity to occur in the beam irradiation period. In the extraction control period, in particular, exhaustion of the accumulated charge of ion beams in the synchrotron greatly affects the uniformity of the dose distribution. Control of the extraction beam current intensity is therefore required in accordance with the accumulated beam charge amount in the synchrotron.

Alternatively, when the accumulated beam charge amount in the synchrotron is greater than the reference value, the predetermined region can be completely irradiated with the beam during the extraction control without exhausting the beam. In this case, however, part of the accumulated beam charge amount in the synchrotron is left unconsumed. This reduces the beam use efficiency; specifically, the accumulated charge of ion beams in the synchrotron is not effectively used for irradiation.

The RMW includes a plurality of wedge-shaped energy absorbers disposed symmetrically about a revolving axis to form a periodic structure. Accordingly, the change with time in the intensity of the beam that passes through the RMW required for forming a desired SOBP changes, that is, the change with time in the beam current intensity during ON control during which the extracted beam passes through the RMW has to be symmetrical so as to match with the symmetrical configuration of the wedge-shaped energy absorbers configured into the periodic structure. At this time, the change with time in the beam current intensity during the extraction beam ON control has only to be linear during the extraction control, and the beam current intensity is not necessarily constant (fixed) at all times. The amplitude feedback control of the radiofrequency signal described in non-patent document 2 allows the extraction beam current intensity to be controlled at a constant (fixed) value during the extraction control period; it is, however, difficult to change the beam current intensity linearly during the extraction control period.

Generally speaking, during control of extraction of ion beams from the synchrotron, the radiofrequency signal with a given intensity level tends more easily to be extracted in the early part of the extraction control, in which the accumulated beam charge amount is high, than in the latter part of the extraction control. Accordingly, in the control method as that described in non-patent document 2, in which the beam current intensity is controlled to be constant at all times during the extraction control, the amplitude of the extraction radiofrequency signal to be fed must be made greater in the latter part than in the early part in order to extract all ion beams accumulated in the synchrotron. This makes it necessary to increase the capacity of an amplifier that feeds the extraction radiofrequency signal at high voltage to the extraction radiofrequency electrode. This leads to an increased equipment cost.

It is therefore a first object of the present invention to provide a charged particle beam irradiation system and a charged particle beam extraction method that can efficiently extract and use accumulated beams in a synchrotron and ensure uniformity of an irradiation dose.

It is a second object of the present invention to provide a charged particle beam irradiation system and a charged particle beam extraction method that can efficiently extract and use accumulated beams in a synchrotron and ensure uniformity of an irradiation dose, and achieve current intensity control for an extraction beam with a simple system configuration.

To achieve the first object, there is provided a charged particle beam irradiation system. The charged particle beam irradiation system includes: detection means for measuring an amount of accumulated charge of ion beams that orbit in a synchrotron immediately before an extraction control period in an operating cycle of the synchrotron; and beam extraction control means for controlling extraction of the ion beams based on the measurement of the accumulated beam charge amount so that extraction of a total of the ion beams is to be completed in time with expiration of an extraction control time (Tex), which represents a length of the extraction control period of the synchrotron and which is set in advance.

This allows the beams accumulated in the synchrotron to be efficiently extracted and used and uniformity of the irradiation dose to be ensured.

Preferably, the irradiation apparatus is structured to operate at a predetermined irradiation cycle (the rotating cycle of the periodic structure of the rotating body for the RMW irradiation method, the circular scanning cycle of the ion beam for the wobbler method, and the scanning cycle of the ion beam for each layer for the raster beam scanning method) and the extraction control time and the irradiation cycle of the irradiation apparatus are set so as to match with each other. The beam extraction control means starts controlling extraction of the ion beams in time with irradiation control performed by the irradiation apparatus after the accumulated beam charge amount has been measured by the accumulated beam charge amount detection means.

The irradiation apparatus includes, for example, a rotating body that has a thickness varying in a rotating direction to thereby vary a level of energy of the ion beam passing therethrough and an object to be irradiated is irradiated with the ion beam that has passed through the rotating body. In this case, preferably, the beam extraction control means includes: first means for generating an ON/OFF signal for controlling extraction and extraction stop of the ion beam from the synchrotron during rotation of the rotating body; second means for finding, with a reference value of the accumulated beam charge amount immediately before the extraction control period in the operating cycle of the synchrotron and with target beam current intensity pattern data associated with the reference value of the accumulated beam charge amount, the reference value and the target beam current intensity pattern data being set in advance, a ratio of a measured value of the accumulated beam charge amount to the reference value of the accumulated beam charge amount after the accumulated beam charge amount has been measured by the accumulated beam charge amount detection means, and correcting the target beam current intensity pattern data according to the above-referenced ratio and a ratio of an actual beam extraction time to the extraction control time to thereby find a target value of the beam current intensity at that particular point in time; and third means for controlling an amplitude of an extraction radiofrequency voltage so as to obtain the target value of the beam current intensity and output timing of the extraction radiofrequency voltage based on the ON/OFF signal.

To achieve the second object, there is provided a charged particle beam irradiation system, in which the irradiation apparatus includes the rotating body. In that system, the target beam current intensity pattern data is set such that the target value of the beam current intensity decreases with time; and the second means finds the target value of the beam current intensity that decreases with time in response to the target beam current intensity pattern data.

This eliminates the need for increasing the amplitude of the extraction radiofrequency signal to be fed in the latter part of the extraction control than in the early part thereof. This, in turn, eliminates the need for increasing the capacity of the amplifier that feeds a high voltage of the extraction radiofrequency signal to an extraction radiofrequency electrode. Current intensity control of the extraction beam can therefore be achieved with a simple arrangement of components.

Further preferably, the beam extraction control means includes: means for calculating a target value of the current intensity of the beam to be extracted from the synchrotron so that extraction of a total of the ion beams that orbit in the synchrotron is to be completed in time with expiration of the extraction control time; means for measuring a beam current intensity actually extracted from the synchrotron; and means for calculating a correction amount of the amplitude of the extraction radiofrequency voltage by using the target value of the beam current intensity and a measured value of the beam current intensity actually extracted.

This allows the control of the amplitude of the extraction radiofrequency voltage to be performed even more accurately and the control of the intensity of the ion beam irradiated on the object to be performed accurately.

In accordance with the aspects of the present invention, the beams accumulated in the synchrotron can be efficiently extracted and used and uniformity of the irradiation dose can be ensured.

In accordance with the aspects of the present invention, current intensity control of the extraction beam can be achieved with a simple arrangement of components.

Further, in accordance with the aspects of the present invention, the control of the amplitude of the extraction radiofrequency voltage can be performed more accurately, and the control of the intensity of the ion beam irradiated on the object can be performed accurately.

BRIEF DESCRIPTION OF THE DRAWINGS

The present invention will be described hereinafter with reference to the accompanying drawings.

FIGS. 4(a) to 4(h) are timing charts of beam extraction control to which the RMW is applied.

DESCRIPTION OF THE PREFERRED EMBODIMENTS

Embodiments of the present invention will be described below.

First Embodiment

A charged particle beam irradiation system and a charged particle beam extraction method according to a first preferred embodiment of the present invention will be described below with reference to FIGS. 1 and 2A and 2B. Note that the charged particle beam irradiation system and the charged particle beam extraction method according to the first embodiment of the present invention are concerned mainly with an ion beam among charged particle beams. Throughout this specification, therefore, the term "beam" represents the "ion beam".

Figure 1:
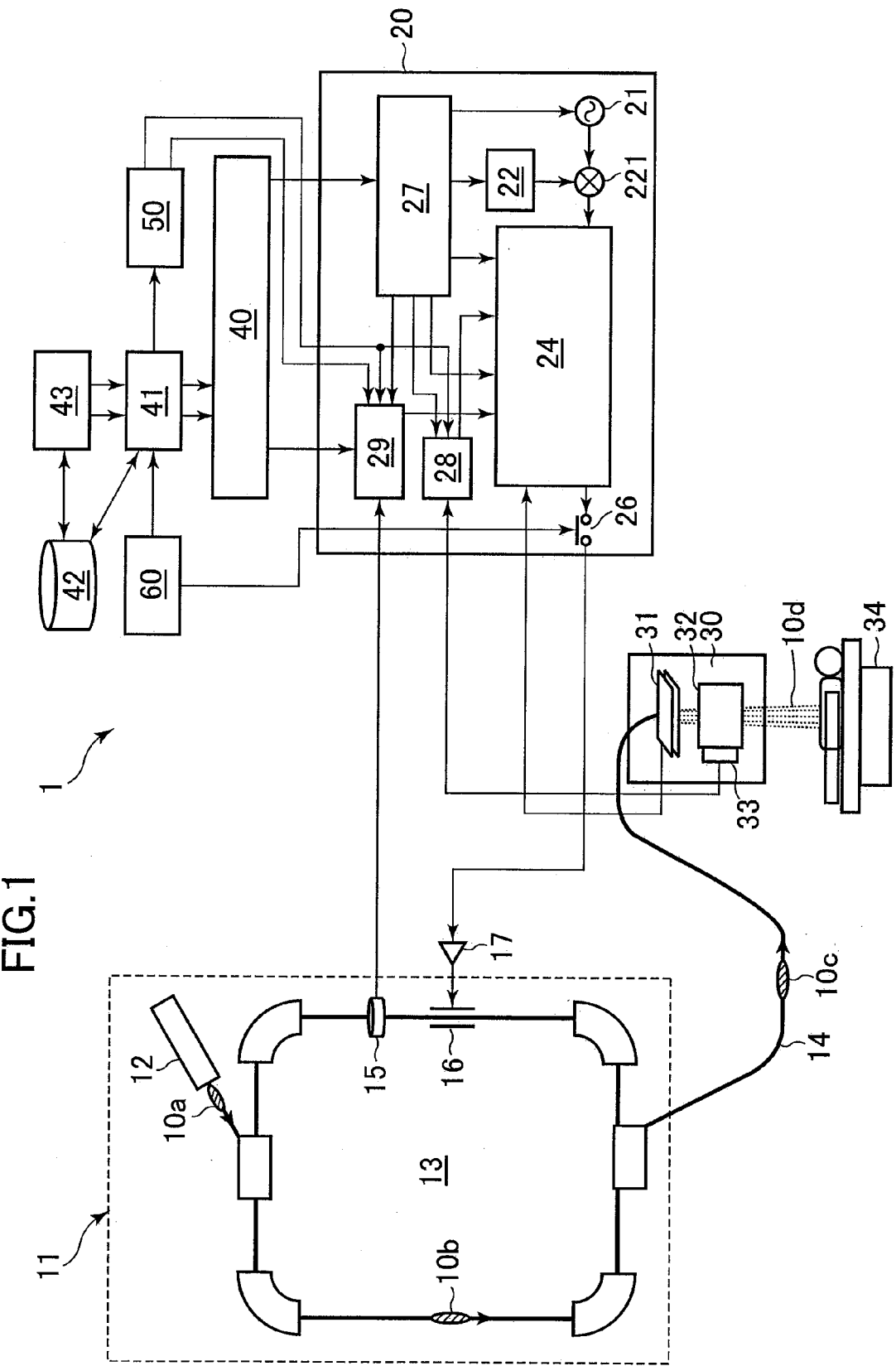
FIG. 1 is a diagram showing an arrangement of a charged particle beam irradiation system according to a first embodiment of the present invention.

Referring to FIG. 1, a charged particle beam irradiation system 1 according to the first embodiment of the present invention includes an ion beam generator 11, a beam transport apparatus 14, and an irradiation field formation apparatus (ion beam irradiation apparatus; hereinafter referred to as the irradiation apparatus) 30. The beam transport apparatus 14 provides communication between the ion beam generator 11 and the irradiation apparatus 30 installed in a therapy room.

A control system for the charged particle beam irradiation system 1 includes an accelerator controller 40, an integrated controller 41, a treatment planning apparatus 43, a storage apparatus 42, a timing system 50, and an interlock system 60. More specifically, the accelerator controller 40 controls the ion beam generator 11 and the beam transport apparatus 14. The integrated controller 41 integrally controls the charged particle beam irradiation system 1. The treatment planning apparatus 43 formulates a plan for beam irradiation conditions for the patient. The storage apparatus 42 stores in memory information planned by the treatment planning apparatus 43 and control information for, for example, the ion beam generator 11 and the beam transport apparatus 14. The timing system 50 achieves synchronization control for the apparatuses that constitute the ion beam generator 11. The interlock system 60 works independently of the integrated controller 41 to ensure utmost safety of the patient. In addition, an extraction controller 20 (beam extraction control means) controls the radiofrequency voltage used when a beam is extracted from the ion beam generator 11 to the beam transport apparatus 14.

The ion beam generator 11 includes an ion source (not shown), a preaccelerator 12, and a synchrotron 13. The ion source is connected to the preaccelerator 2. The preaccelerator 12 is connected to the synchrotron 13. The preaccelerator 12 accelerates an ion beam 10 generated by the ion source to a level of energy on which the ion beam 10 can be incident upon the synchrotron 13. An ion beam 10a accelerated by the preaccelerator 12 is incident upon the synchrotron 13.

Figure 2A:
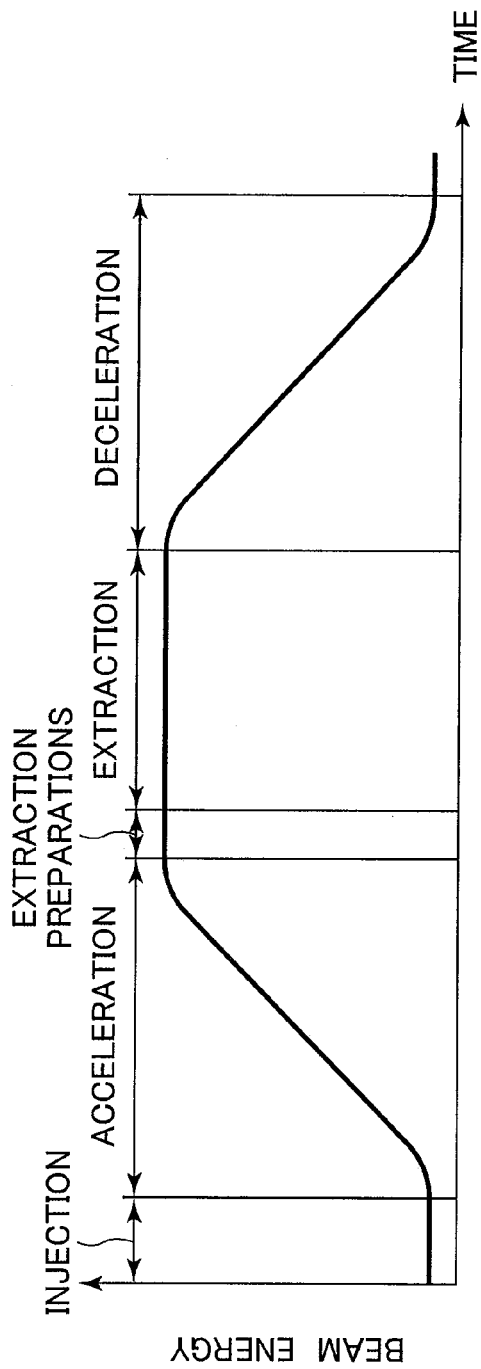
FIGS. 2A and 2B are graphs showing changes in energy of an orbiting beam and in an orbiting beam current intensity in an operating cycle of a synchrotron.

FIG. 2A shows changes in the energy of an orbiting beam in an operating cycle of the synchrotron 13. FIG. 2B shows changes in an amount of charge of the orbiting beam. The synchrotron 13 controls a series of operations including injecting a beam, accelerating the injected beam, extracting the accelerated beam, and decelerating the beam. The synchrotron 13 controls the foregoing operating cycle at a cycle of 2 to 3 seconds. In addition, the synchrotron 13 performs an extraction preparation control before the extraction control.

An ion beam 10b incident upon the synchrotron 13 is accelerated to a desired level of energy by feeding energy thereto using a radiofrequency voltage fed to an acceleration cavity (not shown), while letting the ion beam 10b orbit. At this time, a magnetic field intensity of, for example, a bending magnet (not shown) or a quadrupole magnet (not shown), and the frequency of the radiofrequency voltage fed to the acceleration cavity are increased in response to an increase in the orbiting energy of the ion beam 10b, so that a circular path of the ion beam 10b orbiting inside the synchrotron 13 becomes constant.

The ion beam 10b accelerated to the desired level of energy undergoes the extraction preparation control, so that an excitation amount of the quadrupole magnet and a sextupole magnet (not shown) establishes a condition of enabling extraction of the orbiting beam 10b (stability limit condition of the orbiting beam). After the end of the extraction preparation control, the extraction controller 20 feeds a radiofrequency voltage to an extraction radiofrequency electrode 16 to augment a betatron oscillation amplitude of the beam 10b that orbits within the synchrotron 13. The orbiting beam 10b that exceeds the stability limit condition as a result of the augmentation of the betatron oscillation amplitude is extracted from the synchrotron 13 to the beam transport apparatus 14. Control of extraction of ion beams from the synchrotron 13 can be achieved at high speeds by the extraction controller 20 that performs ON/OFF control of the radiofrequency voltage fed to the extraction radiofrequency electrode 16.

Figure 2B:
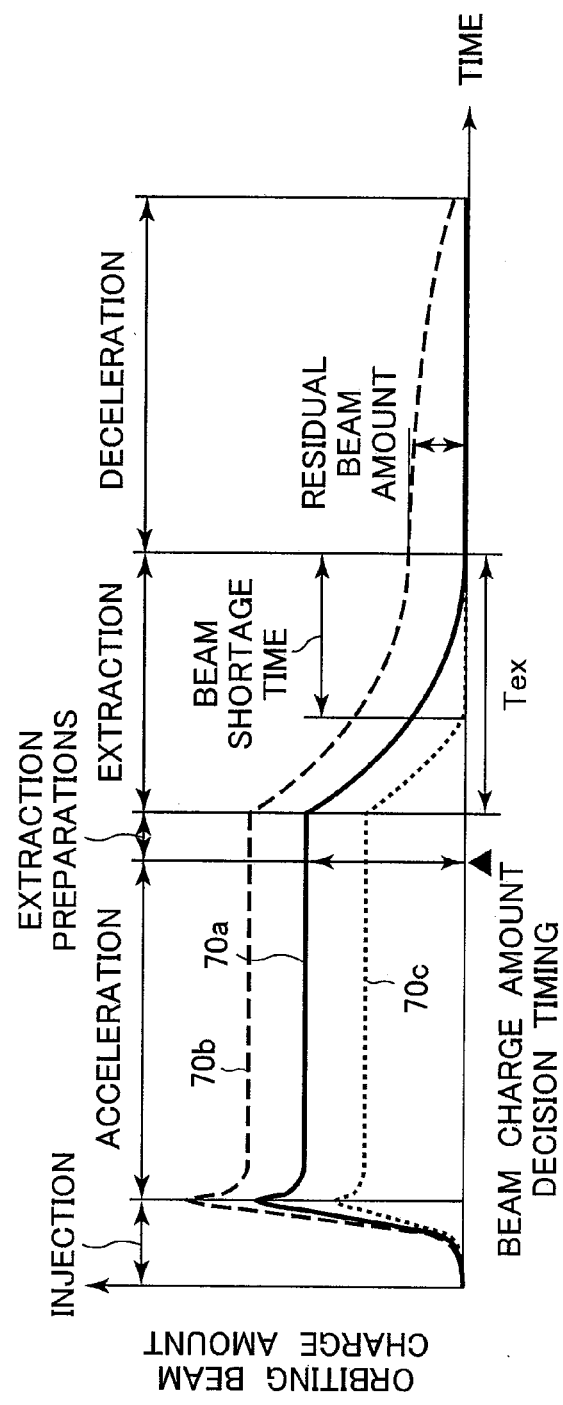

An accumulated beam charge amount 70, the beams orbiting the synchrotron 13, changes as shown in FIG. 2B in accordance with an operation sequence (FIG. 2A) of the synchrotron 13. When the ion beam 10a is incident upon the synchrotron 13, the orbiting beam charge amount gradually builds up. In the early part of an acceleration control, ion beams are lost by a space charge effect or the like, so that the orbiting beam charge amount decays; in the middle to latter part of the acceleration control, however, the orbiting beam charge amount remains substantially constant. In synchrotrons, the orbiting beam charge amount at the end of acceleration is equivalent to the accumulated beam charge amount. By extracting the ion beam 10b from the synchrotron 13, therefore, the intensity of the orbiting beam gradually decays. Ion beams that are not extracted during the extraction control period and are left in the synchrotron 13 are decelerated down to a low energy through the deceleration control performed thereafter before being extinguished.

The amplitude of the radiofrequency voltage fed to the extraction radiofrequency electrode 16 during the beam extraction control is adjusted such that a standard value 70a set for the entire accumulated beam charge amount 70, the beams orbiting the synchrotron 13, can be extracted. When the amount of accumulated charge of ion beams orbiting the synchrotron 13 is more than the standard value 70a (70b of FIG. 2B), therefore, the amplitude of the radiofrequency voltage fed to the extraction radiofrequency electrode 16 must be changed in order to extract all of the orbiting beam charge amount (accumulated beam charge amount) during the extraction control period. If the entire orbiting beam charge amount is not extracted, part of the beams is left and irradiation efficiency of the ion beams cannot be enhanced. Alternatively, when the amount of accumulated charge of ion beams orbiting the synchrotron 13 is less than the standard value 70a (70c of FIG. 2B), the amplitude of the radiofrequency voltage fed to the extraction radiofrequency electrode 16 must be changed. Otherwise, the accumulated beam charge amount will be in short supply in the middle of the extraction control, which results in uneven dose of ion beams irradiated on the affected part. As a result, desired uniformity cannot be ensured in the irradiation zone. To extract the accumulated beam charge amount efficiently and stably, therefore, the amplitude of the radiofrequency voltage fed to the extraction radiofrequency electrode 16 must be adequately controlled according to the accumulated beam charge amount.

A beam 10c extracted from the synchrotron 13 is transported by the beam transport apparatus 14 to the irradiation apparatus 30. In the irradiation apparatus 30, a dose monitor 31 that determines the irradiation dose of a beam 10d with which the patient is irradiated and a beam shape monitor (not shown) are used to determine the dose intensity of the beam 10d with which the patient is irradiated and the beam shape consecutively, so that an RMW 32 forms an SOBP that matches with the thickness of the affected part in a depth direction. The irradiation field that corresponds to the shape of the affected part is formed with the beam for which the SOBP is formed by using a unique jig to be matched with the shape of the patient's affected part, such as a bolus (not shown) or a collimator (not shown).

Figure 3A:
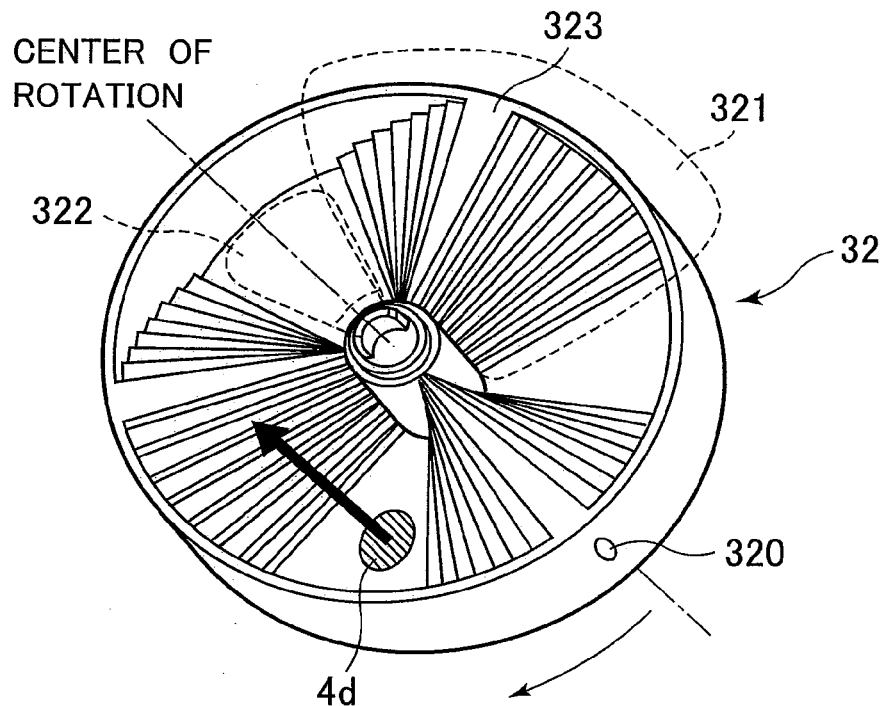
FIGS. 3A and 3B show an arrangement of an RMW and a data structure of RMW gate signal pattern data, respectively.

FIG. 3A shows an arrangement of the RMW 32 that forms a SOBP to be matched with the thickness in the depth direction of the affected part in the patient body. The RMW 32 includes a plurality of vanes (three pairs in accordance with the first embodiment of the present invention) 321 that radially extend from a rotating shaft. Each of these vanes 321 is formed to have a circumferential width that is wider toward a radially outward direction. Each of these vanes 321 has a plurality of planar areas disposed in a stepwise fashion in the circumferential direction of the RMW 32. The thickness between each of the planar areas and a bottom surface of the RMW 32 in the axial direction of the RMW 32 differs from each other. The thickness of a portion of one planar area in the rotating axis direction is referred to as the planar area thickness. A thin vane base 322 is formed between each pair of the vanes 321 in the circumferential direction of the RMW 32. The RMW 32 according to the first embodiment of the present invention has three vane bases (or openings) 322, each being formed between each pair of the vanes 321. The vanes 321 are formed so that the thickness of each planar area increases from the vane bases 322 disposed on both sides of the vanes 321 in the circumferential direction toward the planar area which is positioned on a vane top 323 that is thick in the traveling direction of a beam 4d. The vanes 321 having different thicknesses function as energy absorbers in the RMW 32. As the beam passes through the vanes 321 having varying thicknesses of a rotating RMW 32, energy of the beam extracted from the synchrotron 13 can spread out. Forming a desired SOBP by using the RMW 32 can be achieved by controlling the beam extraction in accordance with the thickness of the vanes 321 of the RMW 32 through which the beam passes. An origin sensor 320 that allows a rotating cycle of the RMW 32 to be observed is disposed on a side surface of the RMW 32.

Figure 3B:
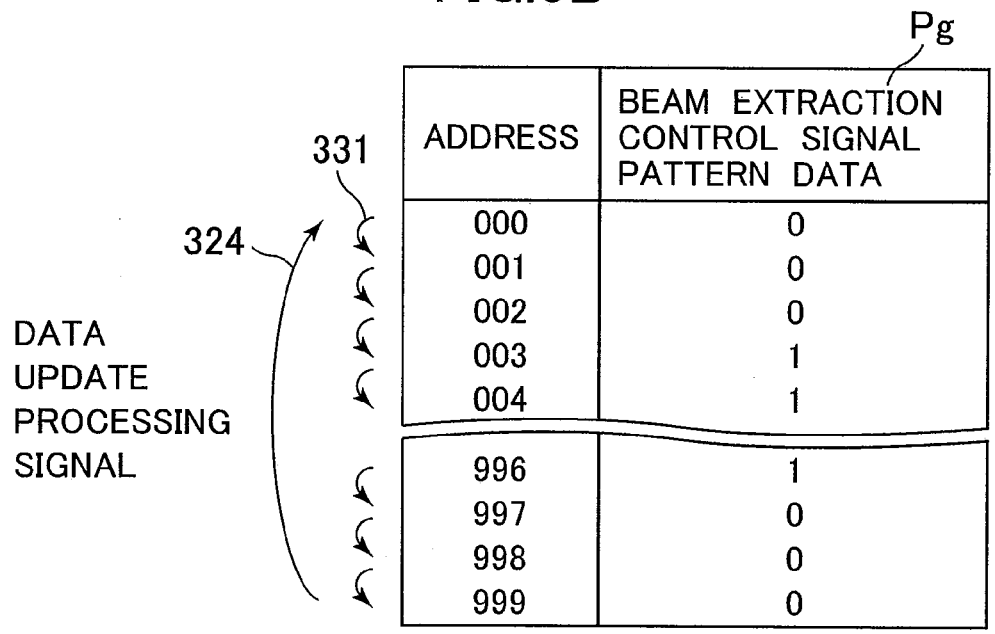

FIG. 3B shows a data structure of an RMW gate signal pattern data Pg. The RMW gate signal pattern data Pg represents digital data that is prepared to be compatible with angular detection resolution for one revolution of the RMW 32, with the data address corresponding to the position indicated by an origin signal outputted from the origin sensor 320 of the RMW 32 as the initial address. The RMW gate signal pattern data Pg uses a "1" to represent data at an angle at which the beam passes when the beam is ON and a "0" to represent data at an angle at which the beam passes when the beam is OFF according to the SOBP formation conditions of the beam to be fired at the patient. The RMW gate signal pattern data Pg is prepared to be matched with the angle at which the beam passes through an area of the RMW 32. A memory address for the RMW gate signal pattern data Pg should therefore permit ring-shaped closed memory access, in which the memory address returns to the initial address each time the RMW 32 rotates one complete turn.

A control method for updating the RMW gate signal pattern data Pg will be described below. The RMW gate signal pattern data Pg is transmitted in advance of the irradiation therapy from the accelerator controller 40 to the extraction controller 20 in accordance with the energy and the SOBP width of the beam with which the patient is irradiated and set in an RMW gate signal processor 28 (part of the beam extraction control means; first means) inside the extraction controller 20. When the RMW 32 rotates, a rotation sensor 33 outputs a rotation detection signal 331 to the RMW gate signal processor 28. The RMW gate signal processor 28 updates addresses of the RMW gate signal pattern data Pg and outputs an RMW gate signal 281 (ON/OFF signal). When the RMW 32 rotates one complete turn, the origin sensor 320 outputs a signal to the RMW gate signal processor 28. In time with an origin signal 324, the RMW gate signal processor 28 updates an address pointer of the RMW gate signal pattern data Pg by replacing a final address with the initial address. The memory address can therefore be assigned in a closed ring form by making available the number of data items for the RMW gate signal pattern data Pg corresponding to the number of rotation detection signals 331 outputted from the rotation sensor 33. The RMW gate signals 281 corresponding to one revolution of the RMW 32 can therefore be easily generated. Through the foregoing operations, control of the required SOBP width and the beam extraction control executed with the rotation of the RMW 32 can be synchronized with each other.

FIGS. 4(a) to 4(h) are timing charts of beam extraction control to which the RMW 32 is applied. As the RMW 32 rotates, the thickness of the vanes 321 at the beam passing position changes timewise (FIG. 4(a)). A rotary encoder, for example, is used for the rotation sensor 33 that detects the angular position of the RMW 32. The rotation sensor 33 outputs about 1000 pulses of the rotation detection signal 331 (FIG. 4(c)) per revolution. Similarly, the origin signal 324 (FIG. 4(b)) is outputted from the origin sensor 320 that observes the rotating cycle of the RMW 32. The RMW gate signal 281 (FIG. 4(d)) is generated based on the rotation detection signal 331 (FIG. 4(c)) from the rotation sensor 33. Note herein that the RMW gate signal 281 (FIG. 4(d)) is used for the ON/OFF control of the beam extraction control in accordance with formation of the desired SOBP. Given a rotation speed of the RMW 32, therefore, a passing time Ta of one cycle of the vane 321 of the RMW 32 and a beam extraction area time Tb are uniquely defined. The three signals of FIGS. 4(b), 4(c), and 4(d) described above are outputted based on rotation of the RMW 32. In the operating cycle of the synchrotron 13, an accumulated beam charge amount detection timing signal 501 (FIG. 4(e)) and an extraction control timing signal 502 (FIG. 4(f)) are outputted in time with an extraction control time Tex. In the RMW irradiation method, the beam irradiation needs to be performed in time with the rotating cycle of the RMW 32. An RMW irradiation gate signal 251 (FIG. 4(g)) is therefore generated from the origin signal 324 inputted for the first time from the RMW 32 since an ON command input of the extraction control timing signal 502 and an OFF command input of the extraction control timing signal 502. A beam extraction control signal 252 (FIG. 4(h)) is outputted through an AND logic of the extraction control timing signal 502, the RMW gate signal 281, and the RMW irradiation gate signal 251 described above. Feeding a radiofrequency signal to the extraction radiofrequency electrode based on this beam extraction control signal 252 allows the patient to be irradiated with the beam 10d of the desired SOBP. The RMW gate signal processor 28 generates these series of beam extraction control signals 252.

Note that a value equaling an integral multiple of the rotating cycle of the vane 321 which is the periodic structure of the RMW 32 is set for the extraction control time Tex so that the extraction control time Tex is in match with the rotating cycle. Specifically, let Trmw be the rotating cycle of each vane 321 of the RMW 32 and n be an integer, then Tex=n·Trmw.

Figure 7:
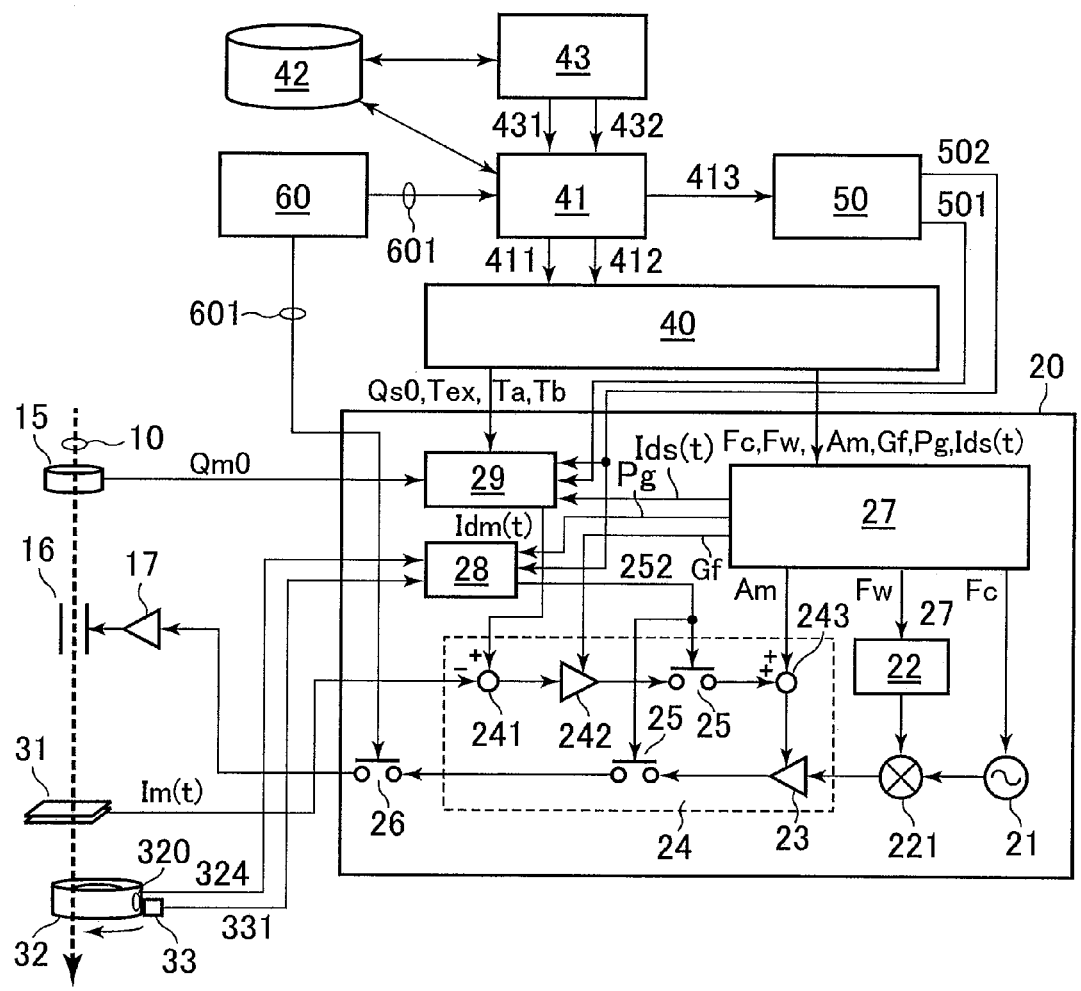
FIG. 7 is a diagram showing an arrangement of an extraction controller when an RMW irradiation method is applied.

FIG. 7 is a diagram showing an arrangement of the extraction controller 20. The extraction controller 20 includes a radiofrequency oscillator 21, a band limit radiofrequency signal generator 22, a radiofrequency mixer 221, a beam current intensity feedback control circuit (hereinafter referred to as the feedback control circuit) 24 (part of the beam extraction control means; third means), a feedback control radiofrequency switch 25 included in the feedback control circuit 24, an interlock signal radiofrequency switch 26, an extraction radiofrequency signal processor 27, a beam extraction control signal generator 28 (i.e., the above RMW gate signal processor 28), and a target beam current intensity correction calculation unit 29 (part of the beam extraction control means; second means).

The extraction controller 20 sets an operating condition of each of the control and calculation units that constitute the extraction controller 20 based on: an extraction-radiofrequency-voltage center frequency Fc, a band-limit-radiofrequency-signal frequency width Fw, an amplitude modulation pattern data Am prepared in advance, a loop gain value Gf of the feedback control circuit 24, the RMW gate signal pattern data Pg controlled in accordance with the rotation angle of the RMW 32 for forming a desired SOBP, and a target beam current intensity waveform pattern data Ids(t), which are transmitted from the accelerator controller 40 to the extraction radiofrequency signal processor 27; and the extraction control time Tex, the passing time Ta and the beam extraction area time Tb of one cycle of the vane 321 of the RMW 32, and a reference value Qs0 of the accumulated beam charge amount before the extraction control, which are transmitted from the accelerator controller 40 to the target beam current intensity correction calculation unit 29. The beam extraction control in time with the operating cycle of the synchrotron 13 is performed based on the accumulated beam charge amount detection timing signal 501 and the extraction control timing signal 502 transmitted from the timing system 50, the rotation detection signal 331 from the rotation sensor 33 that detects the rotating angle of the RMW 32, and the origin signal 324 from the origin sensor 320 that observes the rotating cycle of the RMW 32.

Of the pattern data transmitted from the accelerator controller 40 to the extraction radiofrequency signal processor 27, the amplitude modulation pattern data Am and the target beam current intensity waveform pattern data Ids(t) are time-series data prepared in time with the extraction control time Tex, and the RMW gate signal pattern data Pg is pattern data generated corresponding to a beam passing angle during rotation of the RMW 32.

A control method for the extraction radiofrequency voltage adopted by the extraction controller 20 will be described. The radiofrequency oscillator 21 outputs a radiofrequency signal of the extraction-radiofrequency-voltage center frequency Fc controlled according to energy. The radiofrequency signal output from the radiofrequency oscillator 21 is mixed with a band limit radiofrequency signal outputted from the band limit radiofrequency signal generator 22 by the radiofrequency mixer 221, thereby obtaining a band limit radiofrequency signal with the center frequency Fc and the frequency width Fw. The mixed band limit radiofrequency signal, after being subjected to a control of the amplitude value of the radiofrequency voltage at the feedback control circuit 24 to achieve the beam current intensity waveform (target value of the beam current intensity) obtained by the target beam current intensity correction calculation unit 29, is transmitted to a radiofrequency power amplifier 17 via the interlock signal radiofrequency switch 26 and fed to the extraction radiofrequency electrode 16.

A method for calculating the target beam current intensity performed by the target beam current intensity correction calculation unit 29, as a feature of the present invention, will be described with reference to FIGS. 5(a) to 5(e), 6(a) to 6(e), and 7. FIGS. 5(a) to 5(e) are graphs showing changes with time in the accumulated beam charge amount and the extracted beam current intensity when the RMW gate control is not performed. FIGS. 6(a) to 6(e) are graphs showing changes with time in the accumulated beam charge amount and the extracted beam current intensity when the RMW gate control is performed. FIG. 7 is a diagram showing the arrangement of a feedback control system relative to the extracted beam current intensity.

The reference value Qs0 of the accumulated beam charge amount before the extraction control, the target beam current intensity pattern data (an initial value of the target value is Ids0) when the RMW gate control corresponding to the reference value Qs0 is not performed, the extraction control time Tex, and the passing time Ta and the beam extraction area time Tb of one cycle of the RMW 32 are set in the target beam current intensity correction calculation unit 29 in advance before starting the operation of the synchrotron 13. As described earlier, a value equaling an integral multiple of the rotating cycle of the vane 321 which is the periodic structure of the RMW 32 is set for the extraction control time Tex so that the extraction control time Tex is in match with the rotating cycle. When the operation control of the synchrotron 13 is started, the timing system 50 outputs the accumulated beam charge amount detection timing signal 501 before the operation control shifts from acceleration control to extraction control of the orbiting beam. Using the accumulated beam charge amount detection timing signal 501, a beam current intensity signal Qm0 from an accumulated beam charge amount detection means 15 that measures the beam current intensity of the ion beams accumulated in the synchrotron 13 is measured and the measurement of the beam current intensity signal Qm0 is inputted to the target beam current intensity correction calculation unit 29.

Figure 5:
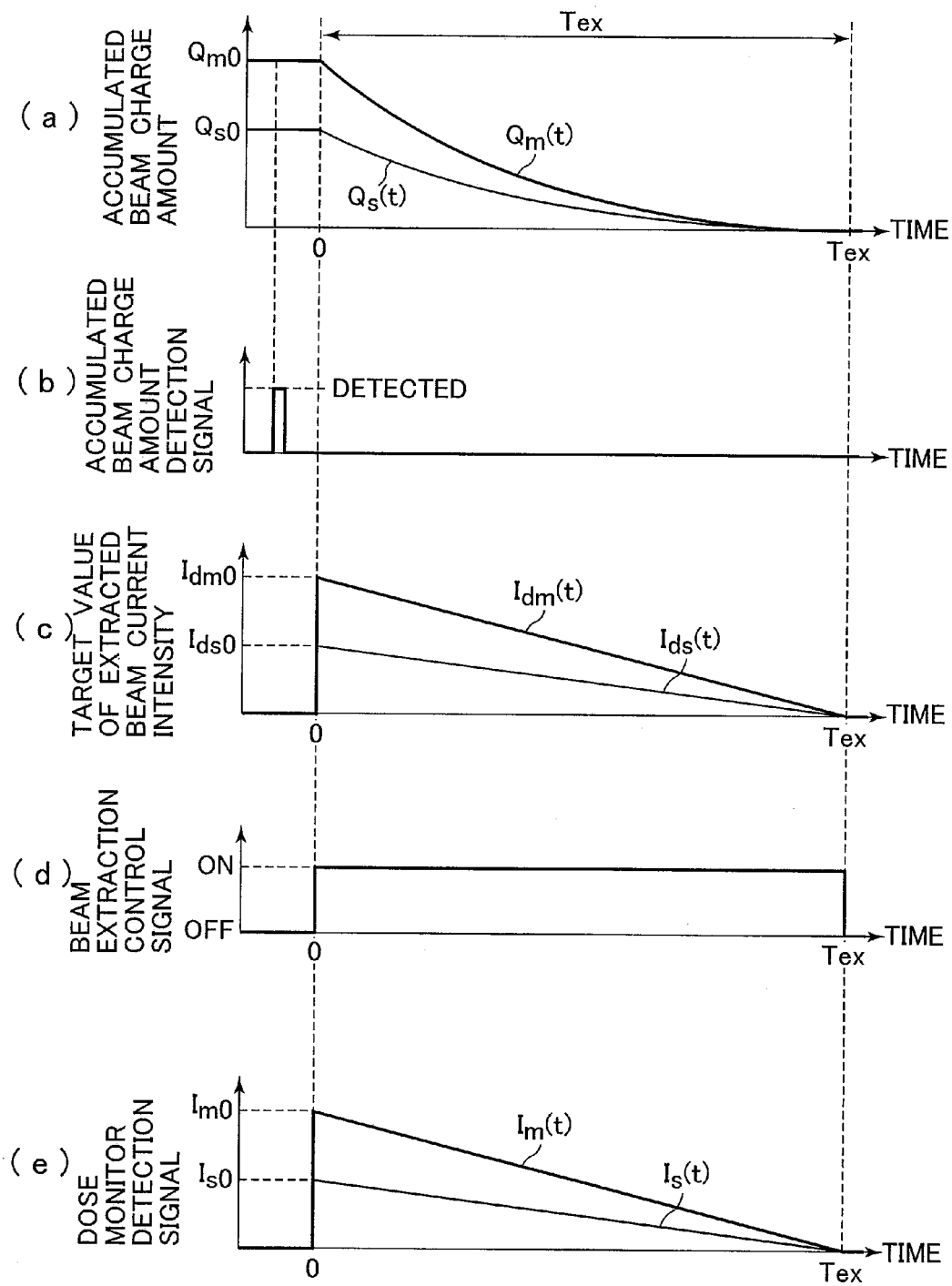
FIGS. 5(a) to 5(e) are graphs showing changes in an accumulated beam charge amount and a dose monitor detection signal when a target value for an extracted beam current intensity is controlled in response to the accumulated beam charge amount.

FIG. 5(a) shows changes with time in the accumulated beam charge amount (Qs(t)) when the accumulated beam charge amount in the synchrotron 13 is the reference value Qs0, and changes with time in the accumulated beam charge amount (Qm(t)) that corresponds to an actual accumulated beam charge amount Qm0. FIG. 5(b) shows timing at which the accumulated beam charge amount in the synchrotron 13 is detected before the start of the extraction control. FIG. 5(c) shows changes with time in the target beam current intensity waveform pattern data Ids(t) and a target beam current intensity pattern data Idm(t) which is obtained by correcting the target beam current intensity waveform pattern data Ids(t) based on the amount of accumulated charge of extraction beams Qm0. FIG. 5(d) shows changes with time in the beam extraction control signal. FIG. 5(e) shows changes with time in the extracted beam current intensity (Is(t)) corresponding to the reference value Qs0 of the accumulated beam charge amount and in the extracted beam current intensity (Im(t)) when the beam current intensity is corrected, as detected by the dose monitor.

In the RMW irradiation method, the beam current has only to change linearly with time during beam extraction control. In the first embodiment of the present invention, therefore, the intensity is made high in the beginnings of acceleration and gradually decreased linearly to 0 at the end of acceleration to ensure that the beams are easily extracted from the synchrotron 13. Specifically, the target beam current intensity waveform pattern data Ids(t) shown in FIG. 5(c) is set such that the target value of the extracted beam current intensity decreases with time and the target value of the extracted beam current intensity obtained from the target beam current intensity pattern data Idm(t) corrected according to the actual accumulated beam charge amount Qm0 also decreases with time corresponding to the target beam current intensity waveform pattern data Ids(t).

An amount of charge of extraction beams Q is the integral of the extraction beam current target value with respect to time. Assuming that the target beam current intensity waveform pattern data Ids(t) shown in FIG. 5(c) is a linear decrease, the condition for extracting all of the reference value Qs0 of the accumulated beam charge amount is Q=Qs0 and the initial value Ids0 of the extraction beam current target value pattern data is expressed by expression 1 below.

$$I_{ds0} = \frac{2Q_{s0}}{T_{ex}} \quad \text{[Expression 1]}$$

Specifically, the initial value Ids0 of the extraction beam current target value pattern data is given by the reference value Qs0 of the accumulated beam charge amount and the extraction control time Tex. Note that expression 2 below is given when the change with time in the extraction beam current target value is fixed, specifically, the extraction beam current is controlled at a constant value.

$$I_{ds0} = \frac{Q_{s0}}{T_{ex}} \quad \text{[Expression 2]}$$

A control method for the extraction beam current target value when the amount of accumulated charge of extracted beams detected based on the accumulated beam charge amount detection timing signal 501 relative to the accumulated beam charge amount Qs0 is Qm0 will be described below. At this time, the control is based on the initial value Ids0 of the extracted beam current intensity target value relative to the accumulated beam charge amount Qs0 and on the extraction control time Tex.

If the accumulated beam charge amount Qs0 is changed to the actual accumulated beam charge amount Qm0, the numerator of expression 1 or 2 may be represented by (Qm0/Qs0). Specifically, when the actual accumulated beam charge amount Qm0 is smaller than the accumulated beam charge amount that serves as the reference value Qs0 (Qm0<Qs0), the initial value Ids0 of the extracted beam current intensity target value is made smaller at a rate of (Qm0/Qs0). The target beam current intensity waveform pattern data Ids(t) is also made smaller at a rate of (Qm0/Qs0) accordingly. Similarly, when the actual accumulated beam charge amount Qm0 is greater than the accumulated beam charge amount that serves as the reference value Qs0 (Qm0>Qs0), the initial value Ids0 of the extracted beam current intensity target value is made greater at a rate of (Qm0/Qs0) and the target beam current intensity waveform pattern data Ids(t) is also made greater at a rate of (Qm0/Qs0) accordingly. In FIG. 5(c), the initial value of the corrected extracted beam current intensity target value is marked Idm0 and the corrected target beam current intensity pattern data is marked Ids(t). All of the accumulated beam charge amount in the synchrotron 13 can be extracted in time with the expiration of the previously set extraction control time Tex by correcting the extracted beam current intensity target value in accordance with the actual accumulated beam charge amount as described above.

Figure 6:
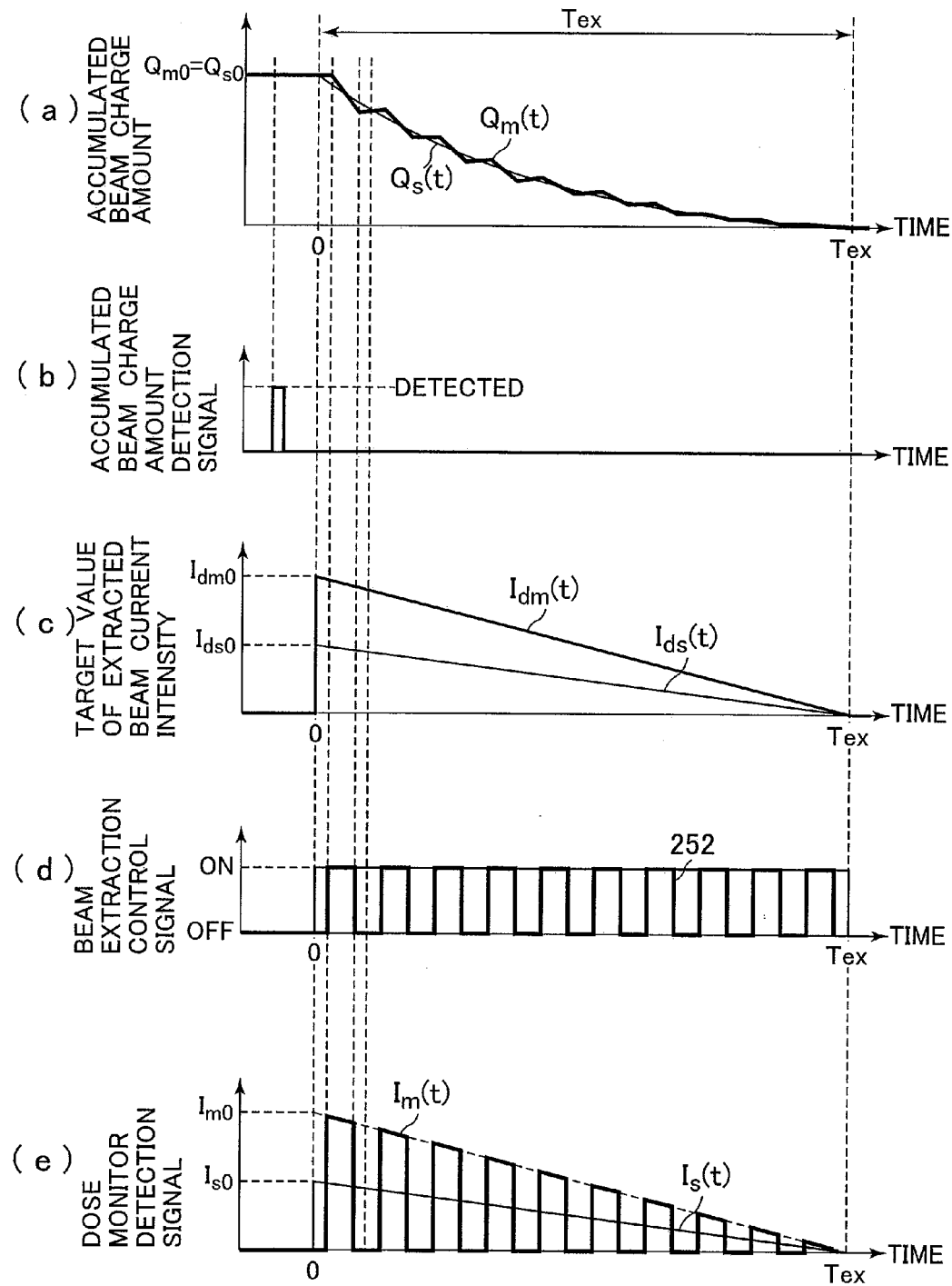
FIGS. 6(a) to 6(e) are graphs showing changes in the accumulated beam charge amount and the dose monitor detection signal when the target value for the extracted beam current intensity is controlled with an effective extraction control time varied by RMW gate control.

Operation when the RMW gate control is performed will next be described with reference to FIGS. 6(a) to 6(e). For ease of description, the accumulated beam charge amount that serves as the reference value Qs0 is equal to the actual accumulated beam charge amount Qm0 (Qm0=Qs0). When the RMW gate control is not performed (Ta=Tb), beams are extracted throughout the entire range relative to the extraction control time Tex. When the RMW gate control is performed using the beam extraction control signal 252 shown in FIG. 6(d) (Ta>Tb), the effective extraction control time becomes Tex (Tb/Ta). Specifically, in the reference value Qs0 of the accumulated beam charge amount, all of the accumulated charge of ion beams of the reference value Qs0 can be extracted when the RMW gate control is not performed; when the RMW gate control is performed, the ion beams equivalent to (Tb/Ta) are left in the synchrotron 13. To extract all of the reference value Qs0 of the accumulated beam charge amount in the synchrotron 13, therefore, the initial value Ids0 of the extracted beam current intensity target value of the pattern data Ids(t) corresponding to the reference value Qs0 of the accumulated beam charge amount is made greater to Idm0 at a rate of (Tb/Ta) as shown in FIG. 6(c). The extracted beam current intensity target value thereafter is also made greater at a rate of (Tb/Ta). All of the accumulated beam charge amount in the synchrotron 13 can be extracted in time with the expiration of the previously set extraction control time Tex by correcting the extracted beam current intensity target value in accordance with the effective extraction control time as described above.

The specific details of control described above will be summarized as follows expressed in expressions 3 and 4.

$$I_{dm}(t) = \alpha \cdot I_{ds}(t) \quad \text{[Expression 3]}$$

$$\alpha = \frac{\left(\frac{Q_{m0}}{Q_{s0}}\right)}{\left(\frac{T_b}{T_a}\right)} \quad \text{[Expression 4]}$$

Where, α is a correction factor and given by expression 4, in which the effective extraction control time relative to the reference extraction control time (Tex) (Tb/Ta) is the denominator and the actual accumulated beam charge amount (Qm0) relative to the reference value Qs0 of the accumulated beam charge amount (Qm0/Qs0) is the numerator. Similarly, the initial value Idm0 of the extracted beam current intensity which is a corrected value of the initial value Ids0 of the extraction beam current target value is expressed by expression 5.

$$I_{dm0} = \frac{\left(\frac{Q_{m0}}{Q_{s0}}\right)}{\left(\frac{T_b}{T_a}\right)} I_{ds0} \quad \text{[Expression 5]}$$

All of the accumulated beam charge amount in the synchrotron 13 can be extracted in time with the expiration of the previously set extraction control time Tex by making corrections shown in expressions 3 and 4 in accordance with the actual accumulated beam charge amount and the effective extraction control time relative to the extracted beam current intensity target value, so that beam use efficiency can be improved.

In addition, the accumulated charge of ion beams in the synchrotron 13 is not exhausted during irradiation, so that uniformity of the irradiation dose can be ensured.

Further, the target beam current intensity waveform pattern data Ids(t) is set such that the target value of the extracted beam current intensity decreases with time (a linear decrease in the first exemplary embodiment of the present invention) and the target value of the extracted beam current intensity obtained from the corrected target beam current intensity pattern data Idm(t) also decreases with time (a linear decrease in the first exemplary embodiment of the present invention). This eliminates the requirement for increasing the amplitude of the extraction radiofrequency signal to be fed in the latter part of the extraction control than in the early part thereof. This, in turn, eliminates the requirement for increasing the capacity of the radiofrequency power amplifier 17 that feeds a high voltage of the extraction radiofrequency signal to the extraction radiofrequency electrode 16. Current intensity control of the extraction beam can therefore be achieved with a simple arrangement of components.

The feedback control method of the extracted beam current intensity will be described with reference to FIG. 7. The feedback control circuit 24 includes an amplitude modulation circuit 23, a deviation calculation circuit 241, a feedback loop gain adjuster 242, an adder circuit 243, and the feedback control radiofrequency switch 25. To describe further some of the foregoing components, the deviation calculation circuit 241 calculates the deviation between a beam current intensity detection value Im(t) from the dose monitor 31 and the target beam current intensity pattern data Idm(t) corrected according to the extraction condition described earlier. The adder circuit 243 adds the amplitude modulation pattern data Am set by the extraction radiofrequency signal processor 27 to a deviation signal inputted via the feedback loop gain adjuster 242. The feedback control radiofrequency switch 25 controls the extraction radiofrequency signal based on the beam extraction control signal 252 outputted from the RMW gate signal processor 28.

When the feedback control of the beam current intensity is performed, the calculation result Idm(t) at the target beam current intensity correction calculation unit 29 is used for the target value of the beam current intensity. The beam 10c extracted from the synchrotron 13 passes through the dose monitor 31 in the irradiation apparatus 30. The dose monitor 31 outputs consecutively a beam current intensity detection signal Im(t) that has passed the dose monitor 31. The deviation calculation circuit 241 of the feedback control circuit 24 calculates deviation of the beam current intensity detection signal Im(t) outputted from the dose monitor 31 from the beam current intensity target value Idm(t). The feedback loop gain adjuster 242 adjusts the deviation calculation result to an appropriate correction amount which is then added to the amplitude modulation pattern data Am of the extraction radiofrequency signal. The amplitude modulation signal having undergone the abovementioned addition is set in the amplitude modulation circuit 23. This allows the beam current intensity of the radiofrequency signal to be controlled to the desired beam current intensity target value Idm(t).

In the first embodiment of the present invention, the beam current intensity target value is corrected relative to the accumulated beam charge amount Qm0 in the synchrotron 13 before the start of the extraction control as described earlier, in order to extract the entire accumulated beam charge amount. It is vital in this case to achieve a stable control of the beam current intensity target value. It is therefore effective to have the feedback control function of the beam current intensity. When it is not feasible to prepare in advance the amplitude modulation pattern data Am, a desired extracted beam current intensity waveform can be obtained even when the amplitude modulation pattern data Am is 0, by having a sufficiently high dynamic range for the feedback control circuit 24.

In the foregoing, the accumulated beam charge amount detection means 15 measures the accumulated beam charge amount Qm0 orbiting inside the synchrotron 13 immediately before the extraction control period in the operating cycle of the synchrotron 13; and the RMW gate signal processor 28, the target beam current intensity correction calculation unit 29, and the feedback control circuit 24 which are included in the extraction controller 20 constitute the beam extraction control means that controls the extraction of the ion beams so that the extraction of the total of the ion beams, as determined based on the measurement Qm0 of the accumulated beam charge amount is completed in time with the expiration of the extraction control time Tex that represents the length of the extraction control period of the synchrotron 13 and that is established in advance.

Further, the RMW gate signal processor 28 of the extraction controller 20 constitutes the first means that generates, during rotation of the RMW (rotating body) 32, the ON/OFF signal 281 for controlling the extraction and extraction stop of the ion beam from the synchrotron 13. The target beam current intensity correction calculation unit 29 constitutes the second means which, with the reference value Qs0 of the accumulated beam charge amount immediately before the extraction control period in the operating cycle of the synchrotron 13 and the target beam current intensity waveform pattern data Ids(t) relative to the reference value Qs0 set in advance, finds the ratio (Qm0/Qs0) of the measurement of the accumulated beam charge amount to the reference value after the measurement of the accumulated beam charge amount by the accumulated beam charge amount detection means 15, and according to this ratio and the ratio (Tb/Ta) of the actual beam extraction time to the extraction control time (Tex), corrects the target beam current intensity waveform pattern data Ids(t) to thereby find the target value of the beam current intensity. The feedback control circuit 24 constitutes the third means that controls the amplitude of the extraction radiofrequency voltage so as to obtain the beam current intensity target value and the output timing of the extraction radiofrequency voltage based on the ON/OFF signal 281.

Additionally, the target beam current intensity correction calculation unit 29 of the extraction controller 20 constitutes means that calculates the target value of the current intensity of the beam to be extracted from the synchrotron 13 so that the extraction of the total of the ion beams orbiting inside the synchrotron 13 is completed in time with the expiration of the extraction control time Tex. The dose monitor 31 constitutes means (current intensity measurement means) that measures the beam current intensity actually extracted from the synchrotron 13. The feedback control circuit 24 constitutes means that calculates the correction amount of the amplitude of the extraction radiofrequency voltage by using the target value of the beam current intensity and the measurement of the beam current intensity actually extracted.

A method of operating the charged particle beam irradiation system to which the present invention is applied will be described below. A doctor inputs patient information (the position and size of the affected part, beam irradiation direction, and the maximum irradiation depth) in the treatment planning apparatus 43. The treatment planning apparatus 43, based on the patient information inputted thereto, uses treatment planning software to calculate various types of data, such as the SOBP width required for the treatment, the irradiation field size, and a target dose for the patient. The treatment planning apparatus 43 further uses the treatment planning software to calculate energy of the beam to be extracted from the synchrotron 13 (extraction energy), the position at which a treatment couch 34 is disposed, and various types of operating parameters such as rotating angles of the RMW 32 at which to start and stop the extraction of the beam. The treatment planning apparatus 43 also selects the RMW 32 appropriate for the treatment. The treatment plan information (including the SOBP width, the irradiation field size, the target dose, various types of operating parameters, the extraction energy, and the selected RMW 32) is inputted to the integrated controller 41 and stored in the storage apparatus 42 of the integrated controller 41.

The treatment plan information is displayed on a display (not shown) disposed in a control room of the therapy room in which preparations for the treatment are being made. A radiological technologist checks what is displayed on the display and places the RMW 32 specified on the display in the irradiation apparatus 30.

A treatment couch controller (not shown) moves, as instructed by the integrated controller 41, the treatment couch 34 on which the patient is fixed and positions the treatment couch 34 so that the affected part of the patient (an object to be irradiated) is located at a point on an extension line of a beam axis. The accelerator controller 40 determines the extraction beam energy by using the treatment plan information supplied from the integrated controller 41 and sets operation control parameters of components that make up the synchrotron 13 and the beam transport apparatus 14. The integrated controller 41, while making preparations for acceleration of the ion beam, outputs an RMW rotation control signal to drive a motor. This causes the RMW 32 to rotate in the direction of an arrow shown in FIG. 3A. The rotation sensor 33 outputs the rotation detection signal 331 according to the rotation of the RMW 32 and the origin sensor 320 outputs the origin signal 324 for each rotating cycle.

The doctor specifies an irradiation start signal for the integrated controller 41 by way of a control panel disposed in the control room. Based on the irradiation start command, the preaccelerator 12 accelerates the ion beam (for example, a proton (or a heavy ion such as a carbon ion)) generated by the ion source and supplies the synchrotron 13 with the ion beam.

The synchrotron 13 accelerates the ion beam 10a injected from the preaccelerator 12 to a desired level of energy by letting the ion beam 10b orbit in the synchrotron 13. The ion beam 10b, after having been accelerated to the target level of energy, is extracted from the synchrotron 13 as the extraction radiofrequency signal is fed to the extraction radiofrequency electrode 16.

The ion beam 10c extracted from the synchrotron 13 travels past the beam transport apparatus 14 to reach the irradiation apparatus 30. The ion beam further travels along a beam path in the irradiation apparatus 30 and moves past the rotating RMW 32, and then the affected part of the patient is irradiated with the ion beam. The dose monitor 31 measures the dose of the ion beam with which the affected part is irradiated. When the irradiation dose of the affected part reaches the target dose value, the measurement of the dose monitor 31 is transmitted to the integrated controller 41. The integrated controller 41 then stops the extraction of the ion beam from the synchrotron 13 to complete the irradiation of the patient with the ion beam 10d.

Should an impediment of some sort that impedes the irradiation of the patient with the beam occur during irradiation control in any of the components that make up the charged particle beam irradiation system 1, the interlock system 60 outputs a signal (fault indicating signal) 601 that indicates that the component is faulty to the extraction controller 20 in parallel with the integrated controller 41. The extraction controller 20 receives the fault indicating signal 601 from the interlock system 60 as a beam extraction stop command and opens the interlock signal radiofrequency switch 26 at once. Opening of the interlock signal radiofrequency switch 26 stops the feeding of the extraction radiofrequency signal to the extraction radiofrequency electrode 16. This allows the synchrotron 13 to achieve the interlock control that stops the extraction of the ion beam 10*b*.

The first embodiment of the present invention can achieve the following effects.

(1) In the first embodiment of the present invention, the amplitude of the extraction radiofrequency voltage is controlled based on the amount of accumulated charge of ion beams orbiting in the synchrotron 13 immediately before the start of the extraction control in the synchrotron 13 and the ratio of the actual extraction control time to the extraction control time in one cycle of operation of the synchrotron 13. All of the accumulated beam charge amount in the synchrotron 13 can thereby be extracted in time with the expiration of the previously set extraction control time Tex. The orbiting beams accumulated in the synchrotron 13 can therefore be efficiently extracted and the beam use efficiency can be improved. In addition, the accumulated charge of ion beams in the synchrotron 13 is not exhausted during irradiation and the beam irradiation is not terminated halfway through the range of angles of the RMW 32 to be irradiated, so that uniformity of the irradiation dose can be ensured.

(2) In the first embodiment of the present invention, the target beam current intensity waveform pattern data Ids(t) is set such that the target value of the extracted beam current intensity decreases with time (a linear decrease in the first exemplary embodiment of the present invention) and the target value of the extracted beam current intensity obtained from the corrected target beam current intensity pattern data Idm(t) also decreases with time (a linear decrease in the first exemplary embodiment of the present invention). This eliminates the requirement for increasing the amplitude of the extraction radiofrequency signal to be fed in the latter part of the extraction control than in the early part thereof. This, in turn, eliminates the requirement for increasing the capacity of the radiofrequency power amplifier 17 that feeds a high voltage of the extraction radiofrequency signal to the extraction radiofrequency electrode 16. Current intensity control of the extraction beam can therefore be achieved with a simple arrangement of components.

(3) In the first embodiment of the present invention, the extracted beam current intensity feedback control is applied as the means for controlling the amplitude of the extraction radiofrequency voltage. The extraction beam current intensity is corrected using the amount of accumulated charge of ion beams orbiting in the synchrotron 13 immediately before the start of the extraction control in the synchrotron 13 and the ratio of the actual extraction control time to the extraction control time in one cycle of operation of the synchrotron 13. The extracted beam current intensity feedback control based on the deviation between the corrected extraction beam current intensity and the beam current intensity detected by the dose monitor 31 is then achieved to enhance accuracy in the extraction beam current control in accordance with the current intensity of the beam orbiting in the synchrotron 13.

(4) In the first embodiment of the present invention, the interlock signal radiofrequency switch 26 for the fault indicating signal 601 from the interlock system 60 and the feedback control radiofrequency switch 25 for the RMW gate are connected in series and independently of each other, so that safety of the patient in beam irradiation can be enhanced.

(5) In the first embodiment of the present invention, arrangements are made such that the RMW 32 is applied for forming the irradiation beam SOBP, the RMW gate signal is prepared so that the beam irradiation is performed only during the irradiation period (Tb) of thickness required for the SOBP formation based on the rotation of the RMW 32, and the RMW gate signal is controlled to be updated based on the rotation detection signal 331 outputted through detection of the rotation of the RMW 32. Update control is therefore performed only during the irradiation period (Tb) in the RMW 32 in the irradiation control period during which the synchrotron 13 extracts ion beams. Control accuracy can therefore be enhanced in accordance with the beam current intensity of the ion beam orbiting in the synchrotron 13.

Second Embodiment

Figure 8:
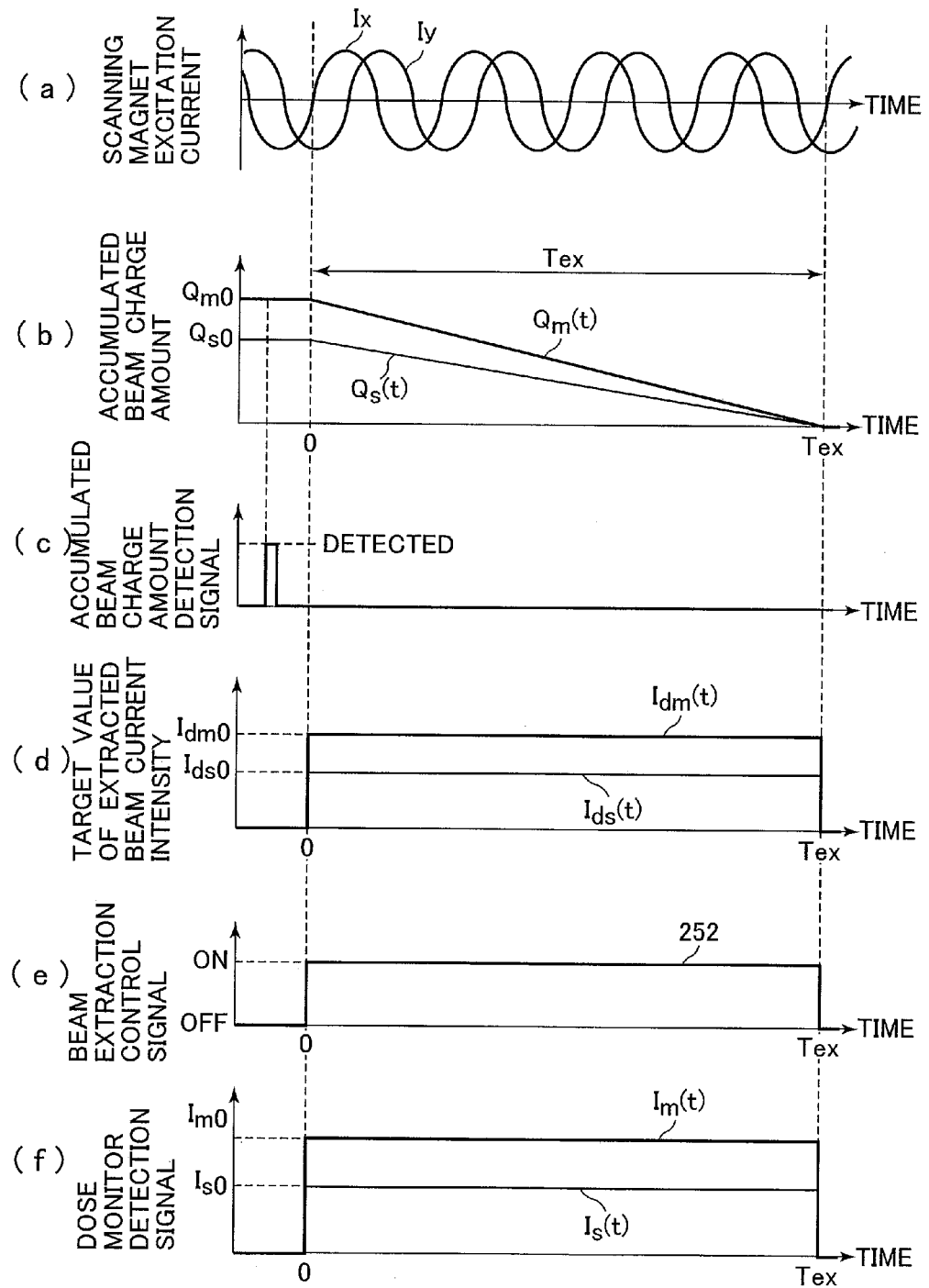
FIGS. 8(a) to 8(f) are graphs showing changes in a scanning magnet excitation current and changes in the accumulated beam charge amount and the dose monitor detection signal when the target value for the extracted beam current intensity is controlled with changing amounts of accumulated charge of ion beams, in a second embodiment of the present invention, in which the present invention is applied to the wobbler method.
Figure 9:
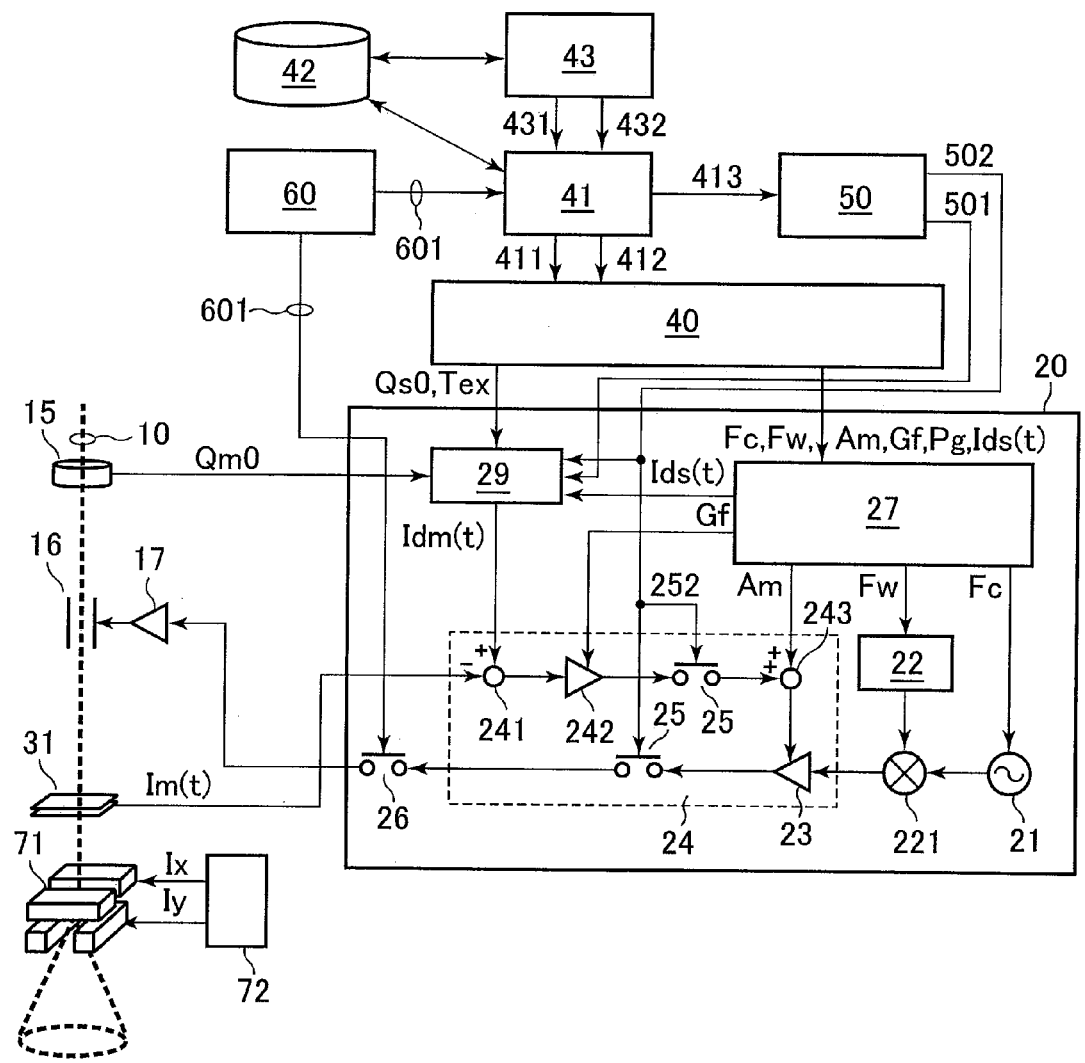
FIG. 9 is a diagram showing an arrangement of an extraction controller in the second embodiment in which the present invention is applied to the wobbler method.
Figure 10:
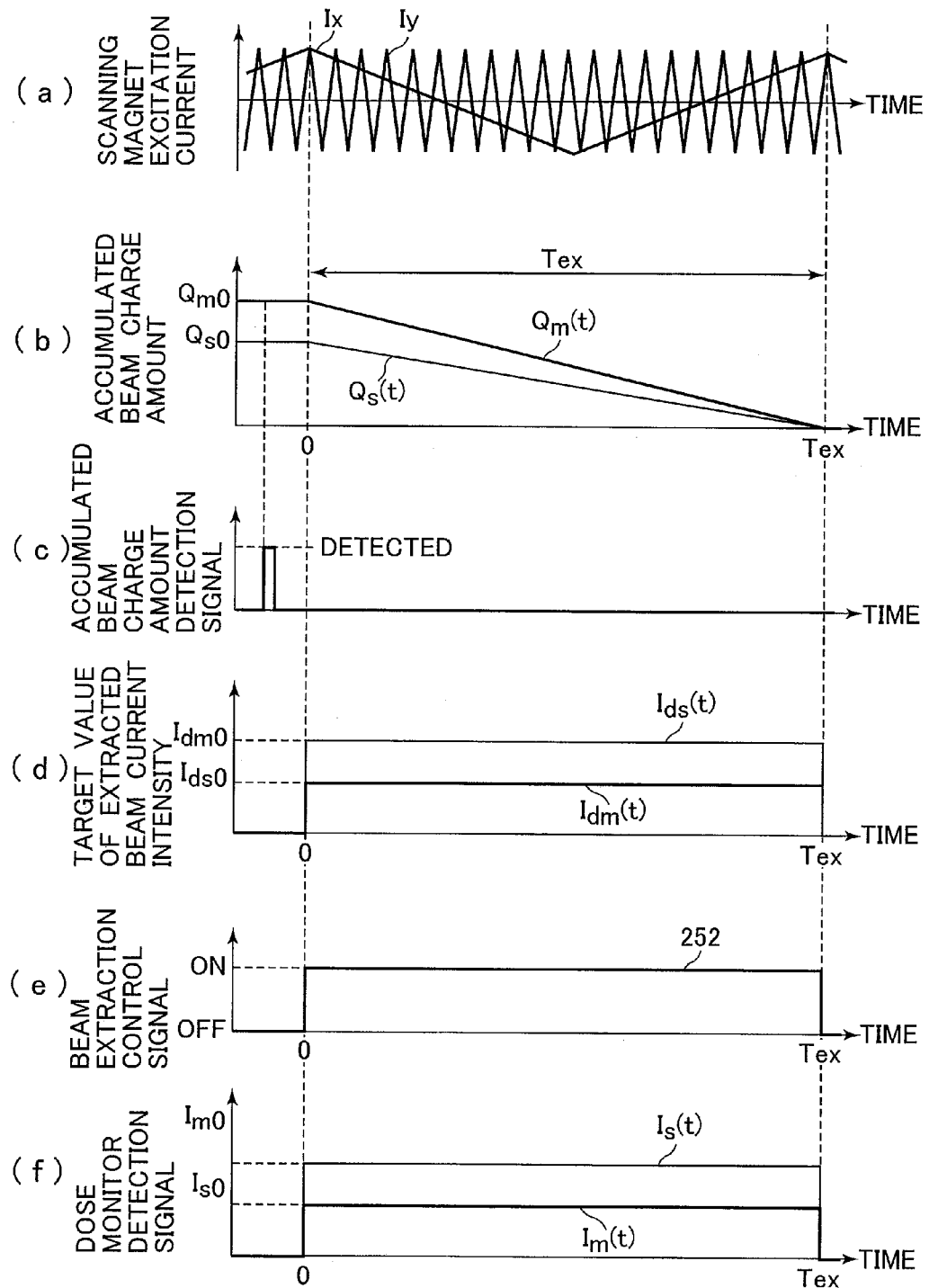
FIGS. 10(a) to 10(f) are graphs showing changes in the scanning magnet excitation current and changes in the accumulated beam charge amount and the dose monitor detection signal when the target value for the extracted beam current intensity is controlled with changing amounts of accumulated charge of ion beams, in a third embodiment of the present invention, in which the present invention is applied to the raster beam scanning method.

A second embodiment of the present invention will be presented. In the second embodiment of the present invention, the wobbler method is adopted for the beam irradiation method. Control of the beam extraction control signal is necessary in time with the scanning cycle of wobbler scanning magnets, while adjusting the extracted beam current intensity to a constant value. Arrangements other than the foregoing are the same as those of the first embodiment shown in FIG. 1. FIGS. 8(*a*) to 8(*e*) are graphs showing changes in a scanning magnet excitation current and changes in the accumulated beam charge amount and the dose monitor detection signal when the target value for the extracted beam current intensity is controlled with changing amounts of accumulated charge of ion beams. FIG. 9 is a diagram showing an arrangement of an extraction controller in the second embodiment in which the present invention is applied to the wobbler method.

The wobbler method uses one set of two wobbler scanning magnets 71 connected to a scanning magnet power source 72. Each of the wobbler scanning magnets 71 is excited by a sine wave current with a phase shift of 90° from each other, so that a scanning trajectory of concentric circles is drawn on a plane of a scatterer to thereby form a uniform SOBP. In the wobbler method, a scanning start phase is made to coincide with a scanning end phase, which ensures uniformity of the plane of the irradiation field. Specifically, when the scanning start and the scanning end are out of phase from each other, the phase shifting produces some parts that are relatively higher or lower in the irradiation dose than others. Therefore, it is necessary to make the scanning start phase coincide with the scanning end phase.

In the second embodiment of the present invention, an extraction control time Tex is specified as a time that is a circular scanning cycle of the scanning magnets multiplied by n and the target value of the extracted beam current intensity is controlled according to the accumulated beam charge amount. This makes the scanning start phase coincide with the scanning end phase at all times, so that uniformity can be ensured on the irradiation plane.

Note herein that the approach to control the target value of the extracted beam current intensity according to the accumulated beam charge amount is the same as that in the first embodiment of the present invention. In the wobbler method, however, the RMW gate control is not performed and thus the correction factor α in expression 4 described earlier is: $\alpha = Qm0/Qs0$. Additionally, the extracted beam current intensity is adjusted to a constant value in the wobbler method, which makes it necessary to have a constant value for the target value of the extracted beam current intensity of the pattern data Ids(t) corresponding to the reference value Qs0 of the accumulated beam charge amount (FIG. 8(*d*)) and the initial value Ids0 of the extracted beam current intensity target value is given by expression 2 cited earlier. This enables extraction of the entire accumulated beam charge amount.

Other extracted beam current intensity control methods are the same as those of the first embodiment of the present invention.

Third Embodiment

Figure 11:
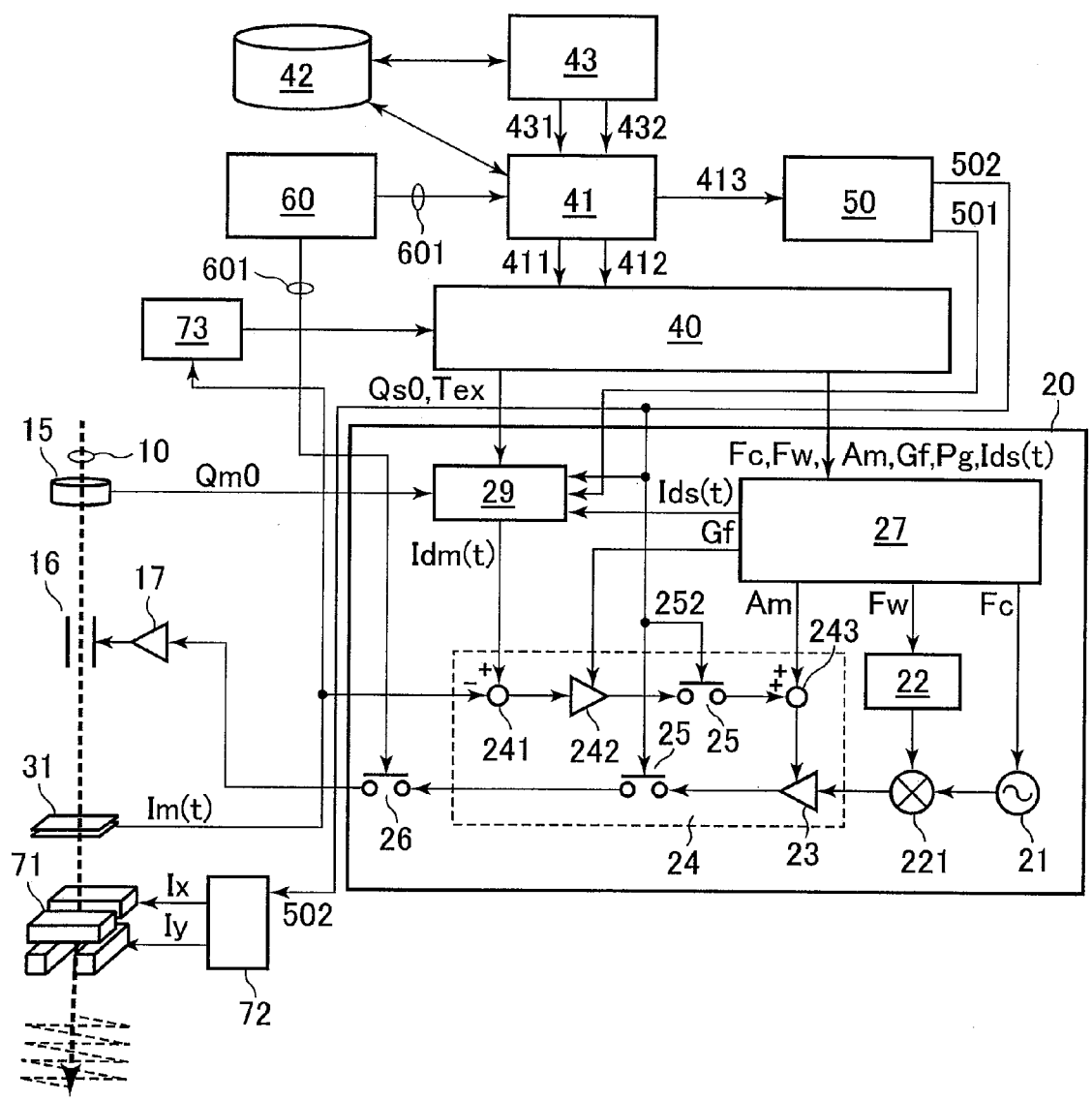
FIG. 11 is a diagram showing an arrangement of an extraction controller in the third embodiment in which the present invention is applied to the raster beam scanning method.

A third embodiment of the present invention will be presented. The third embodiment of the present invention incorporates the raster beam scanning method for the beam irradiation method, and control for scanning while adjusting the extracted beam current intensity to a constant value is necessary. For the third embodiment of the present invention, a control method will be described, in which no gate control is performed during the beam extraction control. Other arrangements are the same those of the first embodiment of the present invention shown in FIG. 1. FIGS. 10(a) to 10(f) are graphs showing changes in the scanning magnet excitation current and changes in the accumulated beam charge amount and the dose monitor detection signal when the target value for the extracted beam current intensity is controlled with changing amounts of accumulated charge of ion beams, in which the present invention is applied to the raster beam scanning method. FIG. 11 is a diagram showing an arrangement of an extraction controller in the third embodiment in which the present invention is applied to the raster beam scanning method.

In the raster beam scanning method, the affected part is directly and continuously irradiated with a beam without using a scatterer, so that uniformity on the plane of irradiation can be ensured by controlling to maintain a constant beam current intensity during irradiation. In addition, in the raster beam scanning method, the affected part is divided into a plurality of layers in the affected part depth direction and the energy of the ion beam extracted from the synchrotron 13 is varied according to a beam range required for each of the plurality of layers, so that a desired dose can be given to each layer.

To form a desired SOBP with an integrated value of a dose with which each layer is irradiated when the raster beam scanning method is applied, it is necessary to make the dose with which each layer is irradiated high for a deep layer (=the layer to be irradiated with a beam of high energy) and low for a shallow layer (=the layer to be irradiated with a beam of low energy). Preferably in this case, the irradiation beam current intensity is made high for the deep layer and low for the shallow layer in order to shorten the treatment irradiation time and increase the irradiation efficiency. Accordingly, it is necessary to adjust the extracted beam current intensity, the beam being extracted from the synchrotron 13, according to the energy required for each layer.

Further, in the raster beam scanning method, the irradiation zone of one layer is irradiated repeatedly an integral multiple number of times, which ensures dose uniformity within the irradiation zone. The reason for this control is that the affected part is directly irradiated with the beam in the raster beam scanning method, which makes it necessary to provide treatment in which controlling the uniformity of the irradiation dose is performed even more accurately than in the irradiation method using a scatterer. Control is therefore applied for ensuring uniformity of the irradiation dose by irradiating with the desired dose in a plurality of sequences, not at one time. When the beam current intensity being extracted from the synchrotron 13 is exhausted before the completion of irradiation of one layer of the irradiation zone, therefore, variations in dose uniformity can occur within the irradiation zone. Consequently, the extracted beam current intensity must be controlled such that one layer of the scanning zone can be irradiated in the operating cycle of the synchrotron 13 with an intensity not exceeding the target dose for each layer, the target dose being set by the treatment plan.

In the third embodiment of the present invention, the integrated controller 41 sets the energy of the beam and the irradiation dose for each layer to be irradiated in the accelerator controller 40 based on the treatment plan information set from the treatment planning apparatus 43. The accelerator controller 40 includes means for controlling the target value of the extracted beam current intensity according to the irradiation dose for each layer and another means for transmitting the target value of the extracted beam current intensity to the extraction controller 20 each time the energy is changed.

In response to a command to start the irradiation therapy for the patient, the beam is extracted from the synchrotron 13. Raster scanning magnets 71 in the irradiation apparatus use the extraction control timing signal 502 as a control trigger signal to scan the irradiation plane in a zigzag single stroke while the extraction control timing signal 502 is being input. The dose monitor 31 detects the irradiation beam current intensity Im(t) which, in turn, is outputted to the extraction controller 20 and an irradiation dose integrating circuit 73, respectively. Note that, in accordance with the third embodiment of the present invention, the output from the dose monitor 31 is supplied to the extraction controller 20 and the irradiation dose integrating circuit 73. It is nonetheless possible to configure an arrangement, in which a dose monitor 31 is independently provided for each of the extraction controller 20 and the irradiation dose integrating circuit 73.

The extraction controller 20 performs control so as to provide the extracted beam current intensity that is transmitted from the accelerator controller 40 within the extraction control time Tex. When, at this time, the accumulated beam charge amount Qm0 in the synchrotron 13 is more than the reference value Qs0, the extraction beam intensity control is performed based on the pattern data Ids(t) that corresponds to the reference value Qs0 of the amount of accumulated charge of ion beams transmitted from the accelerator controller 40 with the correction factor $\alpha$ set as $\alpha=1$ of expression 4 cited earlier. When the accumulated beam charge amount Qm0 in the synchrotron 13 is less than the reference value Qs0, on the other hand, the correction factor $\alpha$ of expression 4 cited earlier is set as $\alpha=Qm0/Qs0$ and control is thereby performed to keep the target value of the extracted beam current intensity low according to the accumulated beam charge amount in the synchrotron 13. The beam can thereby be used efficiently, while ensuring uniformity of the irradiation dose of the beam extracted in all operating cycles of the synchrotron 13. The controls performed as described above inhibit beam irradiation of the target dose or more, so that the extracted beam current intensity can be stably supplied at all times during raster beam scanning.

The irradiation dose integrating circuit 73 integrates the irradiation dose for each layer and, when the desired dose is reached, transmits an energy change command to the accelerator controller 40. Based on the energy change command transmitted from the irradiation dose integrating circuit 73, the accelerator controller 40 updates the initial value Ids0 of the target pattern data of the extracted beam current intensity (Ids(t)) in the extraction controller 20, together with the beam energy supplied from the synchrotron 13. The desired dose can be accurately fed to each layer of the affected part, by changing the target value of the extracted beam current intensity together with the beam energy as described above.

In the first through third embodiments described heretofore, the extraction control time Tex is defined to be matched with the irradiation cycle of the irradiation apparatus (the rotating cycle of the rotating body for the RMW irradiation method, the circular scanning cycle of the ion beam for the wobbler method, and the scanning cycle of the ion beam for each layer for the raster beam scanning method) when the extraction control time Tex and the irradiation cycle are to be set so as to be mutually matched with each other. The irradiation apparatus may be controlled by defining the extraction control time Tex to be a predetermined value based on another condition and defining the irradiation cycle of the irradiation apparatus to be matched with the extraction control time Tex.

What is claimed is:

1. A charged particle beam irradiation system, comprising:
a synchrotron which accelerates an ion beam, wherein the ion beam is extracted from the synchrotron;
an irradiation apparatus for irradiating an object to be irradiated with the ion beam introduced from the synchrotron;
detection means for measuring an amount of accumulated charge of the ion beam that orbits in the synchrotron immediately before an extraction control period in an operating cycle of the synchrotron; and
beam extraction control means for controlling extraction of the ion beam based on the measurement result of the accumulated beam charge amount so that extraction of a total amount of the ion beam is to be completed with an expiration of an extraction control time, the extraction control time representing a length of the extraction control period of the synchrotron and being set in advance, wherein:
the irradiation apparatus is structured to operate at a predetermined irradiation cycle, and
the beam extraction control means sets a value of the integral multiple of the irradiation cycle of the irradiation apparatus for the extraction control time such that an end of the extraction control time occurs at an end of a last irradiation cycle of the irradiation apparatus that occurs within the extraction control time.

2. The charged particle beam irradiation system according to claim 1, wherein
the irradiation apparatus includes a rotating body that has a plurality of periodic structures, each of the periodic structures having a thickness that varies in a rotating direction to thereby vary a level of energy of the ion beam passing therethrough, and irradiates the object to be irradiated with the ion beam that has passed through the periodic structure of the rotating body; and
the irradiation cycle of the irradiation apparatus corresponds to a rotating cycle of each periodic structure of the rotating body.

3. The charged particle beam irradiation system according to claim 1, wherein
the irradiation apparatus includes wobbler scanning magnets and irradiates the object to be irradiated with the ion beam while scanning the object circularly by the wobbler scanning magnets, and
the irradiation cycle of the irradiation apparatus corresponds to a circular scanning cycle of the ion beam by the wobbler scanning magnets.

4. The charged particle beam irradiation system according to claim 1, wherein
the irradiation apparatus includes raster scanning magnets and irradiates each layer in a depth direction of the object to be irradiated with the ion beam while scanning the object zigzag by the raster scanning magnets, and
the extraction control time and a scanning cycle of the ion beam for each layer by the raster scanning magnets are set so as to match with each other.

5. The charged particle beam irradiation system according to claim 1, wherein
the beam extraction control means starts controlling extraction of the ion beam in synchronism with irradiation control performed by the irradiation apparatus after the accumulated beam charge amount has been measured by the detection means.

6. The charged particle beam irradiation system according to claim 1, wherein
the beam extraction control means has set therein a reference value of the accumulated beam charge amount immediately before the extraction control period in the operating cycle of the synchrotron and target beam current intensity pattern data associated with the reference value of the accumulated beam charge amount in advance; and
the beam extraction control means finds, after the accumulated beam charge amount has been measured by the detection means, a ratio of a measured value of the accumulated beam charge amount to the reference value of the accumulated beam charge amount, corrects the target beam current intensity pattern data according to the ratio to thereby find a target value of the beam current intensity at that particular point in time, and controls an amplitude of an extraction radiofrequency voltage so as to obtain the target value of the beam current intensity.

7. The charged particle beam irradiation system according to claim 1, wherein
the irradiation apparatus includes a rotating body that has a thickness varying in a rotating direction to thereby vary a level of energy of the ion beam passing therethrough and irradiates the object to be irradiated with the ion beam that has passed through the rotating body, and
the beam extraction control means includes:
first means for generating an ON/OFF signal for controlling extraction and extraction stop of the ion beam from the synchrotron during rotation of the rotating body;
second means which has set therein a reference value of the accumulated beam charge amount immediately before the extraction control period in the operating cycle of the synchrotron and target beam current intensity pattern data associated with the reference value of the accumulated beam charge amount in advance, the second means finding a ratio of a measured value of the accumulated beam charge amount to the reference value of the accumulated beam charge amount after the accumulated beam charge amount has been measured by the detection means, and correcting the target beam current intensity pattern data according to the above-referenced ratio and a ratio of an actual beam extraction time to the extraction control time to thereby find a target value of the beam current intensity at that particular point in time; and
third means for controlling an amplitude of an extraction radiofrequency voltage so as to obtain the target value of the beam current intensity and output timing of the extraction radiofrequency voltage based on the ON/OFF signal.

8. The charged particle beam irradiation system according to claim 7, wherein
the target beam current intensity pattern data is set such that the target value of the beam current intensity decreases with time, and
the second means finds the target value of the beam current intensity that decreases with time in response to the target beam current intensity pattern data.

9. The charged particle beam irradiation system according to claim 1, wherein
the beam extraction control means includes:
means for calculating a target value of the current intensity of the beam to be extracted from the synchrotron so that extraction of a total of the ion beam that orbit in the synchrotron is to be completed in time with expiration of the extraction control time;
means for measuring a beam current intensity actually extracted from the synchrotron; and
means for calculating a correction amount of the amplitude of the extraction radiofrequency voltage by using the target value of the beam current intensity and a measured value of the current intensity of the beam actually extracted.

10. The charged particle beam irradiation system according to claim 1, wherein the beam extraction control means includes means for controlling an amplitude of an extraction voltage according to the measurement result of the accumulated beam charge amount.

11. The charged particle beam irradiation system according to claim 1, wherein
the irradiation apparatus includes raster scanning magnets and irradiates each layer in a depth direction of the object to be irradiated with the ion beam while scanning the object zigzag by the raster scanning magnets, and
the extraction control time and a scanning cycle of the ion beam for each layer by the raster scanning magnets are set so as to match with each other.

12. A charged particle beam extraction method for extracting from a synchrotron an ion beam that is accelerated while orbiting in the synchrotron and introducing the ion beam to an irradiation apparatus, the method comprising:
a first step of setting in advance an extraction control time that is a length of an extraction control period in an operating cycle of the synchrotron;
a second step of measuring an amount of accumulated charge of the ion beam that orbits in the synchrotron immediately before the extraction control period in the operating cycle of the synchrotron; and
a third step of controlling the ion beam so that extraction of a total amount of the ion beam is to be completed with an expiration of the extraction control time based on the measurement result of the accumulated beam charge amount,
wherein:
the irradiation apparatus is structured to operate at a predetermined irradiation cycle, and
the first step sets a value of an integral multiple of the irradiation cycle of the irradiation apparatus for the extraction control time such that an end of the extraction control time occurs at an end of a last irradiation cycle of the irradiation apparatus that occurs within the extraction control time.

13. The charged particle beam extraction method according to claim 12, wherein
the third step starts controlling extraction of the ion beam in synchronism with irradiation control performed by the irradiation apparatus after the accumulated beam charge amount has been measured.

14. The charged particle beam extraction method according to claim 12, wherein
the first step further sets in advance a reference value of the accumulated beam charge amount immediately before the extraction control period in the operating cycle of the synchrotron and target beam current intensity pattern data associated with the reference value of the accumulated beam charge amount, and
the third step finds, after the accumulated beam charge amount has been measured, a ratio of a measured value of the accumulated beam charge amount to the reference value of the accumulated beam charge amount, corrects the target beam current intensity pattern data according to the ratio to thereby find a target value of the beam current intensity at that particular point in time, and controls an amplitude of an extraction radiofrequency voltage so as to obtain the target value of the beam current intensity.

15. The charged particle beam extraction method according to claim 12, wherein
the irradiation apparatus includes a rotating body that has a thickness varying in a rotating direction to thereby vary a level of energy of the ion beam passing therethrough and irradiates an object to be irradiated with the ion beam that has passed through the rotating body,
the first step further sets in advance a reference value of the accumulated beam charge amount immediately before the extraction control period in the operating cycle of the synchrotron and target beam current intensity pattern data associated with the reference value of the accumulated beam charge amount, and
the third step comprises:
a fourth step of generating an ON/OFF signal for controlling extraction and extraction stop of the ion beam from the synchrotron during rotation of the rotating body;
a fifth step of finding, after the accumulated beam charge amount has been measured, a ratio of a measured value of the accumulated beam charge amount to the reference value of the accumulated beam charge amount, and correcting the target beam current intensity pattern data according to the above-referenced ratio and a ratio of an actual beam extraction time to the extraction control time to thereby find a target value of the beam current intensity at that particular point in time; and
a sixth step of controlling an amplitude of an extraction radiofrequency voltage so as to obtain the target value of the beam current intensity and controlling output timing of the extraction radiofrequency voltage based on the ON/OFF signal.

16. The charged particle beam extraction method according to claim 15, wherein
the first step sets the target beam current intensity pattern data such that the target value of the beam current intensity decreases with time, and
the fourth step finds the target value of the beam current intensity that decreases with time in response to the target beam current intensity pattern data.

17. The charged particle beam extraction method according to claim 12, wherein the third step of controlling the ion beam includes controlling an amplitude of an extraction voltage according to the measurement result of the accumulated beam charge amount.

18. A charged particle beam irradiation system, comprising:
a synchrotron which accelerates an ion beam, wherein the ion beam is extracted from the synchrotron;
an irradiation apparatus for irradiating an object to be irradiated with the ion beam introduced from the synchrotron;
a detector which measures an amount of accumulated charge of the ion beam that orbits in the synchrotron immediately before an extraction control period in an operating cycle of the synchrotron; and a beam extraction controller which controls extraction of the ion beam based on the measurement result of the accumulated beam charge amount so that extraction of a total amount of the ion beam is to be completed with an expiration of an extraction control time, the extraction control time representing a length of the extraction control period of the synchrotron and being set in advance, wherein:

the irradiation apparatus is structured to operate at a predetermined irradiation cycle, and the beam extraction controller sets a value of the integral multiple of the irradiation cycle of the irradiation apparatus for the extraction control time such that an end of the extraction control time occurs at an end of a last irradiation cycle of the irradiation apparatus that occurs within the extraction control time.

19. The charged particle beam irradiation system according to claim 18, wherein the irradiation apparatus includes a rotating body that has a plurality of periodic structures, each of the periodic structures having a thickness that varies in a rotating direction to thereby vary a level of energy of the ion beam passing therethrough, and irradiates the object to be irradiated with the ion beam that has passed through the periodic structure of the rotating body; and the irradiation cycle of the irradiation apparatus corresponds to a rotating cycle of each periodic structure of the rotating body.

20. The charged particle beam irradiation system according to claim 18, wherein the irradiation apparatus includes wobbler scanning magnets and irradiates the object to be irradiated with the ion beam while scanning the object circularly by the wobbler scanning magnets, and the irradiation cycle of the irradiation apparatus corresponds to a circular scanning cycle of the ion beam by the wobbler scanning magnets.

21. The charged particle beam irradiation system according to claim 18, wherein the beam extraction controller starts controlling extraction of the ion beam in synchronism with irradiation control performed by the irradiation apparatus after the accumulated beam charge amount has been measured by the detector.

22. The charged particle beam irradiation system according to claim 18, wherein the beam extraction controller has set therein a reference value of the accumulated beam charge amount immediately before the extraction control period in the operating cycle of the synchrotron and target beam current intensity pattern data associated with the reference value of the accumulated beam charge amount in advance; and the beam extraction controller finds, after the accumulated beam charge amount has been measured by the detector, a ratio of a measured value of the accumulated beam charge amount to the reference value of the accumulated beam charge amount, corrects the target beam current intensity pattern data according to the ratio to thereby find a target value of the beam current intensity at that particular point in time, and controls an amplitude of an extraction radiofrequency voltage so as to obtain the target value of the beam current intensity.

23. The charged particle beam irradiation system according to claim 18, wherein the irradiation apparatus includes a rotating body that has a thickness varying in a rotating direction to thereby vary a level of energy of the ion beam passing therethrough and irradiates the object to be irradiated with the ion beam that has passed through the rotating body, and the beam extraction controller includes:

first means for generating an ON/OFF signal for controlling extraction and extraction stop of the ion beam from the synchrotron during rotation of the rotating body;

second means which has set therein a reference value of the accumulated beam charge amount immediately before the extraction control period in the operating cycle of the synchrotron and target beam current intensity pattern data associated with the reference value of the accumulated beam charge amount in advance, the second means finding a ratio of a measured value of the accumulated beam charge amount to the reference value of the accumulated beam charge amount after the accumulated beam charge amount has been measured by the detector, and correcting the target beam current intensity pattern data according to the above-referenced ratio and a ratio of an actual beam extraction time to the extraction control time to thereby find a target value of the beam current intensity at that particular point in time; and third means for controlling an amplitude of an extraction radiofrequency voltage so as to obtain the target value of the beam current intensity and output timing of the extraction radiofrequency voltage based on the ON/OFF signal.

24. The charged particle beam irradiation system according to claim 23, wherein the target beam current intensity pattern data is set such that the target value of the beam current intensity decreases with time, and the second means finds the target value of the beam current intensity that decreases with time in response to the target beam current intensity pattern data.

25. The charged particle beam irradiation system according to claim 18, wherein the beam extraction controller includes:

means for calculating a target value of the current intensity of the beam to be extracted from the synchrotron so that extraction of a total of the ion beam that orbit in the synchrotron is to be completed in time with expiration of the extraction control time;

means for measuring a beam current intensity actually extracted from the synchrotron; and means for calculating a correction amount of the amplitude of the extraction radiofrequency voltage by using the target value of the beam current intensity and a measured value of the current intensity of the beam actually extracted.

26. The charged particle beam irradiation system according to claim 18, wherein the beam extraction controller controls an amplitude of an extraction voltage according to the measurement result of the accumulated beam charge amount.

* * * * *